(12) United States Patent
Brenes et al.

(10) Patent No.: US 10,493,057 B2
(45) Date of Patent: Dec. 3, 2019

(54) ACETOGENIN MOLECULES HAVING ANTIPLATELET AND/OR ANTITHROMBIC ACTIVITIES, AND METHODS AND COMPOSITIONS THEREOF

(71) Applicant: INSTITUTO TECNOLOGICO Y DE ESTUDIOS SUPERIORES DE MONTERREY, Monterrey, Nuevo Leon (MX)

(72) Inventors: Carmen Hernandez Brenes, Monterrey (MX); Gerardo de Jesus Garcia Rivas, Monterrey (MX); Guillermo Torre Amione, Monterrey (MX); Dariana Graciela Rodriguez Sanchez, Monterrey (MX)

(73) Assignee: INSTITUTO TECNOLOGICO Y DE ESTUDIOS SUPERIORES DE MONTERREY, Monterrey, Nuevo Leon (MX)

( * ) Notice: Subject to any disclaimer, the term of this patent is extended or adjusted under 35 U.S.C. 154(b) by 0 days.

(21) Appl. No.: 15/580,933

(22) PCT Filed: Sep. 23, 2015

(86) PCT No.: PCT/IB2015/002021
§ 371 (c)(1),
(2) Date: Dec. 8, 2017

(87) PCT Pub. No.: WO2017/051208
PCT Pub. Date: Mar. 30, 2017

(65) Prior Publication Data
US 2018/0161305 A1   Jun. 14, 2018

(51) Int. Cl.
*A61K 31/365* (2006.01)
*A61P 7/02* (2006.01)

(52) U.S. Cl.
CPC ............. *A61K 31/365* (2013.01); *A61P 7/02* (2018.01); *A61K 2300/00* (2013.01)

(58) Field of Classification Search
CPC ..... C07C 69/007; C07C 69/01; A61K 31/365; A61P 7/02
See application file for complete search history.

(56) References Cited

U.S. PATENT DOCUMENTS

| | | |
|---|---|---|
| 2,550,254 A | 4/1951 | Jensen |
| 5,217,950 A | 6/1993 | Blackburn et al. |
| 5,458,876 A | 10/1995 | Monticello |
| 5,468,490 A | 11/1995 | Huber et al. |
| 5,498,411 A | 3/1996 | Rancurel |
| 5,573,797 A | 11/1996 | Wilhoit |
| 5,573,800 A | 11/1996 | Wilhoit |
| 5,573,801 A | 11/1996 | Wilhoit |
| 6,057,366 A * | 5/2000 | Seawright .............. A61K 31/22 514/546 |
| 6,133,313 A | 10/2000 | Thomson et al. |
| 6,326,364 B1 | 12/2001 | Lin et al. |
| 6,582,688 B1 | 6/2003 | Broutin et al. |
| 6,620,446 B2 | 9/2003 | King et al. |
| 7,101,913 B2 * | 9/2006 | Arimoto ................ A61K 36/54 424/769 |
| 7,862,842 B2 | 1/2011 | Beltran et al. |
| 9,422,504 B2 * | 8/2016 | Msika ..................... A61K 36/54 |
| 9,962,344 B2 * | 5/2018 | Baron .................. A61K 9/2054 |
| 2004/0122095 A1 | 6/2004 | Bonaventura et al. |
| 2005/0170027 A1 | 8/2005 | Arimoto et al. |
| 2006/0062813 A1 | 3/2006 | Adachi et al. |
| 2006/0099323 A1 | 5/2006 | Piccirilli et al. |
| 2009/0163590 A1 | 6/2009 | Msika et al. |
| 2010/0034944 A1 * | 2/2010 | Beyazova ............... A23L 27/88 426/534 |
| 2011/0217251 A1 * | 9/2011 | Meretzki .............. A61K 31/047 424/59 |
| 2011/0250154 A1 | 10/2011 | Meretzki et al. |
| 2012/0071551 A1 | 3/2012 | Mesina et al. |

(Continued)

FOREIGN PATENT DOCUMENTS

| | | | |
|---|---|---|---|
| CA | 494110 A | 6/1953 | |
| GB | 1421129 A * | 1/1976 | ............. C07C 17/16 |

(Continued)

OTHER PUBLICATIONS

D. Prusky, 72 Plant Disease, 381-384 (1988) (Year: 1988).*
L. Karni et al., 35 Physiological and Molecular Plant Pathology, 367-374 (1989) (Year: 1989).*
I. Kobiler et al., 43 Physiological and Molecular Plant Pathology, 319-328 (1993) (Year: 1993).*
S. Bittner et al., 10 Phytochemistry (Elsevier), 1417-1421 (1971) (Year: 1971).*
S. Gazit et al., 27 Physiologia Plantarum, 77-82 (1972) (Year: 1972).*
H. Hashimura et al., 65 Bioscience, Biotechnology, and Biochemistry, 1656-1658 (2001) (Year: 2001).*
H. Kawagishi et al., 49 Journal of Agricultural and Food Chemistry, 2215-2221 (2001) (Year: 2001).*

(Continued)

*Primary Examiner* — Alexander R Pagano
(74) *Attorney, Agent, or Firm* — Pepper Hamilton LLP

(57) ABSTRACT

The present disclosure relates, according to some embodiments, to acetogenin molecules that may have antiplatelet and/or antithronibic activities. In some embodiments, the present disclosure relates to an acetogenin molecule selected from the group comprising: Acetogenin 1, Acetogenin 2, Acetogenin 3, Acetogenin 4, Acetogenin 5, Acetogenin 6, Acetogenin 7, Acetogenin 8, Acetogenin 9, Acetogenin 10, Acetogenin 11, Acetogenin 12, Acetogenin 13, and Acetogenin 14. The present disclosure relates in some embodiments to a pharmaceutical composition comprising a first acetogenin molecule and a delivery vehicle, wherein the first acetogenin molecule is selected from the group comprising: Acetogenin 1, Acetogenin 2, Acetogenin 3, Acetogenin 4, Acetogenin 5, Acetogenin 6, Acetogenin 7, Acetogenin 8, Acetogenin 9, Acetogenin 10, Acetogenin 11, Acetogenin 12, Acetogenin 13, and Acetogenin 14.

14 Claims, 10 Drawing Sheets

(56) References Cited

U.S. PATENT DOCUMENTS

| | | | |
|---|---|---|---|
| 2012/0201884 A1 | 8/2012 | Gokaraju et al. | |
| 2012/0294887 A1 | 11/2012 | Saunois et al. | |
| 2013/0216488 A1* | 8/2013 | Hernandez-Brenes | ..................... A61K 31/12 424/59 |
| 2016/0249613 A1* | 9/2016 | Hernandez-Brenes | ..................... A61K 31/12 424/59 |
| 2017/0055526 A1* | 3/2017 | Hernandez-Brenes | ..................... A61K 31/12 |
| 2018/0103671 A1* | 4/2018 | Hernandez-Brenes | ..................... A61K 8/36 |

FOREIGN PATENT DOCUMENTS

| | | | |
|---|---|---|---|
| JP | 2001097828 A | 10/2001 | |
| JP | 2002053474 A | 2/2002 | |
| JP | 2003509506 A | 11/2003 | |
| JP | 2008156240 A | 7/2008 | |
| JP | 2009164558 A | 7/2009 | |
| WO | 9522969 A1 | 8/1953 | |
| WO | 2010/00744 A2 | 1/2010 | |
| WO | 2010026596 A2 | 3/2010 | |

OTHER PUBLICATIONS

O. Kim et al., 64 Bioscience, Biotechnology, and Biochemistry, 2500-2503 (2000) (Year: 2000).*
O. Kim et al., 64 Bioscience, Biotechnology, and Biochemistry, 2504-2507 (2000) (Year: 2000).*
O. Kim et al., 48 Journal of Agricultural and Food Chemistry, 1557-1563 (2000) (Year: 2000).*
C. Chang et al., 39 Agricultural and Biological Chemistry, 1167-1168 (1975) (Year: 1975).*
L. Neeman et al., 19 Applied Microbiology, 470-473 (1970) (Year: 1970).*
D. Rodriguez-Sanchez et al., 6 Food & Function, 192-202 (2015) (Year: 2015).*
Y. Kashman et al., 7 Israel Journal of Chemistry, 173-176 (1969).*
Rodriguez-Sanchez, D. G. et al. "Isolation and chemical identification of lipid derivatives from avocado (*Persea americana*) pulp with antiplatelet and antithrombotic activities." Food & Function, vol. 6, 2015, pp. 193-203.
International Search Report and Written Opinion dated Apr. 21, 2016 in PCT/IB2015/002021 (7 pgs.).
Chen et al., "Bacteriocins and Their Food Applications," Comprehensive Reviews in Food Science and Food Safety 2(3):82-100 (2003).
Davidson et al., "Antimicrobials in Food," Third Edition, CRC Press, Taylor & Francis Group, Boca Raton, Florida (2005).
Hara-Kudo et al., "Antibacterial Action on Pathogenic Bacterial Spore by Green Tea Catechins," Journal of the Science of Food and Agriculture 85:2354-2361 (2005).
Pierson et al., "Nitrite, Nitrite Alternatives, and the Control of Clostridium Botulinum in Cured Meats," Critical Reviews in Food Science and Nutrition 17(2):141-187 (1983).
Tsukiyama et al., "Antibacterial Activity of Licochalcone A Against Spore-Formng Bacteria," Antimicrobial Agents and Chemotherapy 46(5):1226-1230 (2002).
Castillo-Juarez et al., "Anti-Helicobacter Pylori Activity of Plants Used in Mexican Traditional Medicine for Gastrointestinal Disorders," J. Ethnopharmacol. 122:402-405 (2009).
Hurtado et al., "*Staphylococcus aureus*: Revision of the Mechanisms of Pathogenicity and Physiopathology of Staphylococcal Infections," Rev. Soc. Venez. Microbiol. 22:112-118 (2002) (abstract only).
Leite et al., "Chemical Composition, Toxicity and Larvicidal and Antifungal Activities of *Persea americana* (Avocado) Seed Extracts," Rev. Soc. Bras. Med. Trop. 42(2):110-113 (2009).

Prusky et al., "The Relationship Between Antifungal Diene Levels and Fungal Inhibition During Quiescent Infection of Unripe Avocado Fruits by Colletotrichum gloeosporioides," Plant Pathol. 40:45-52 (1991).
Raymond-Chia et al., "Antimicrobial Activity of Crude Epicarp and Seed Extracts from Mature Avocado Fruit (*Persea Americana*) of Three Cultivars," Pharm. Biol. 48:753-756 (2010).
Sivanathan et al., "Biological Activity of Four Antifungal Compounds in Immature Avocado," J. Phytopat. 125:97-109 (1989).
Notice of Reasons for Rejection for Japanese Patent Application 2013-523692 dated Jul. 12, 2016.
Medicinal Chemistry of Natural Products, Nankodo Co., Ltd., pp. 139-141 (2004).
Prusky et al., "Regulation of Natural Resistance of Avocado Fruit for the Control of Postharvest Disease," Proc. of Second World Avocado Congress, pp. 479-484 (1992).
Subsequent Substantive Examination Report for Philippines Patent Application No. 1/2013/500258 dated Jan. 30, 2017.
Office Action for Canadian Patent Application No. 2,807,779 dated Oct. 2, 2017.
Office Action for European Application No. 14176098.3-1454 dated Dec. 13, 2017.
Office Action for Philippines Patent Application No. 1/2013/500258 dated Jan. 5, 2018.
Carman et al., "A Further Synthesis of an Analogue of the Antifungal/Antiherbivore Lipid and Avocado," Aust. J. Chem. 51:955-959 (1998).
Restriction Requirement for U.S. Appl. No. 13/763,262 dated Mar. 3, 2015.
Office Action for U.S. Appl. No. 13/763,262 dated Jun. 5, 2015.
Ciarciaglini et al., "Germination-Induced Bioluminescence, a Route to Determine the Inhibitory Effect of a Combination Preservation Treatment on Bacterial Spores," Applied and Envirmonmental Microbiology 66 (9):3735-3742 (2000).
Heyndrickx, M., "The Importance of Endospore-Forming Bacteria Originating from Soil for Contamination of Industrial Food Processing," Applied and Environmental Soil Science 2011 Article ID 561975 11 pages (2011).
Prusky et al., "Identification of an Antifungal Compound in Unripe Avocado Fruits and its Possible Involvement in the Quiescent Infections of Colletotrichum Gloeosporioides," J. Phytopathology 132: 319-327 (1991).
Jackson et al., "Survival and Growth of Clostridium Perfringens in Commercial No-Nitrate-or-Nitrite-Added (Natural and Organic) Frankfurters, Hams, and Bacon," Journal of Food Protection 74:3 410-416 (2011).
Knapp et al., "Bactericidal Effects of Polyunsaturated Fatty Acids," The Journal of Infectious Diseases 154:1 84-94 (1986).
Slepecky R. and Hemphill E., "The Genus Bacillus-Nonmedical," pp. 530-562 in the Prokaryotes (M. Dworkin, S. Falkow, E. Rosenberg, K. Schleifer, and E. Stackenbrandt eds., 3d ed. 2006).
Office Action for Canadian Patent Application No. 2,807,779 dated Jun. 4, 2018.
First Office Action for China Patent Application No. 201610773165.1 dated May 9, 2018 (English Translation).
Office Action for Philippines Patent Application No. 1/2013/500258 dated Jun. 8, 2018.
European Office Action for European Patent Application Serial No. 14176098.3 (dated Jan. 28, 2019).
Chinese Office Action for Chinese Patent Application Serial No. 201610773165.1 (dated Jan. 23, 2019).
Office Action Restriction Requirement for U.S. Appl. No. 15/148,712 (dated Oct. 9, 2018).
Office Action for U.S. Appl. No. 15/148,712 (dated Feb. 11, 2019).
Office Action for U.S. Appl. No. 15/348,740 (dated Feb. 11, 2019).
Prusky, "Further Evidence for the Involvement of a Preformed Antifungal Compound in the Latency of Colletotrichum Gloeosporioides on Unripe Avocado Fruits," Physiol. Plant Pathol. 22:189-98 (1983).
International Search Report, PCT/IB2011/053535, dated Aug. 3, 2012, 4 pages.
Yang, H., et al., "Supercritical fluid CO2 extraction and simultaneous determination of eight annonaceous acetogenins in Annona

(56) References Cited

OTHER PUBLICATIONS genus plant seeds by HPLC-DAD method," Journal of Pharmaceutical and Biomedical Analysis, vol. 49, (2009), pp. 140-144.
Ugbogu, O.C., et al., "Short Communication: The antimicrobial effect of oils from Pentaclethra macrophylla Bent, Chrysophyllum albidum G Don and Persea gratissima Gaerth F on some local clinical bacteria isolates," African Journal of Biotechnology, vol. 8 (2), pp. 285-287, Jan. 19, 2009.
Sugiyama, T., et al., "Synthesis of All Four Stereoisomers of Antibacteria Component of Avocado," Agric. Biol Chem., vol. 46 (2), pp. 481-485 (1982).
Smola, M., Thesis, "Contribution a l'etude de la formulation et de l'analyse physiochimique de formulations pediatriques microemulsionnees," Unviersite Louis Pastuer Strasbourg I, 2007, 297 pages (English portions included within text).
Rodriguez-Saona, C., et al., "Growth Inhibitory, Insecticidal, and Feeding Deterrent Effects of (12Z, 15Z)-1-Acetoxy-2-Hydroxy-4-Oxo-Heneicosa-12, 15-Diene, A Compound from Avocado Fruit to Spodoptera exigua," Journal of Chemical Ecology, vol. 23, No. 7, (1997), 13 pages.
Rodriguez Carpena, J-G, et al. "Avocado (*Persea americana* Mill.) Phenolics, In Vitro Antioxidant and Antimicrobial Activities, and Inhibition of Lipid and Protein Oxidation in Porcine Patties," Journal of Agricultural and Food Chemistry, vol. 59, (2011), pp. 5625-5635.
Rayman, M.K., et al., "Nisin: a Possible Alternative or Adjunct to Nitrite in the Preservation of Meats," Applied and Environmental Microbiology, vol. 41, No. 2, Feb. 1981, pp. 375-380.
Ramos-Jerz, M., et al., Dissertation, Phytochemical Analysis of Avocado Seeds (*Persea americana* Mill., C.v. Hass), published by Cuvillier Verlag, Oct. 16, 2007, 159 pages.
Prusky, D., et al., "Possible Involvement of an Antifungal Diene in the Latency of Colletotrichum gloeosporioides on Unripe Avocado Fruits," Phytopathotogy, Vo 72, pp. 1578-1582 (1982).
Padron, J.M., et al., "Beta-Hydroxy-alpha. Beta-unsaturated ketones: A new Pharmacophore for the design of anticancer drugs," Bioorganic & Medicinal Chemistry Letters, vol. 16, (2006), pp. 2266-2269.
Oberlies, N.H., et al., "Cytotoxic and Insecticidal Constituents of the Unripe Fruit of Persea americana," J. Nat. Prod., vol. 61, (1998), pp. 781-785.
Neeman, I., et al., "New Antibacterial Agent Isolated from the Avocado Pear," Applied Microbiology, vol. 19, No. 3, Mar. 1970, pp. 470-473.
Murakoshi, S., et al., "Effects of Two Components from the Avocado Leaves (*Perseea americana* Mill.) and the Related Compounds on the Growth of Silkworm Larvae, *Bombyx mori* L.," Jap. J. appl. Ent. Zool. vol. 20, pp. 87-91, (1976), Abstract in English.
Maseko, R.B., "Synthesis of Authentic Organic Standards of Antibacterial Compounds Isolated from Avocados," Dissertation, Department of Chemistry and Physics Faculty of Natural Sciences, Tshwane University of Technology, May 2006, 106 pages.
Macleod, J.K., et al., "A Short Enantioselective Synthesis of a Biologically Active Compound from Persea Americana" Journal of Natural Products, vol. 58, No. 8, pp. 1270-1273, Aug. 1995.
Leon, L.G. et al., "beta-Hydroxy-alpha, beta-unsaturated ketones. A new pharmacophore for the design of anticancer drugs, Part 2," ChemMedChem, vol. 3, (2008), pp. 1740-1747.
Kim, O.K., et al., "Novel Nitric Oxide and Superoxide Generation Inhibitors, Persenone A and B, from Avocado Fruit," J Agric Food Chem , vol. 48, (2000), pp. 1557-1563.
Kim, O.K. et al, "Inhibition by (−)-Persenone A-related Compounds of Nitric Oxide and Superoxide Generation from Inflammatory Leukocytes," Biosci Biotechnol Biochem , vol. 64, No. 1, pp. 2500-2503 (2000).
Kim, O.K , et al., An Avocado Constituent, Persenone A, Suppresses Expression of Inducible Forms of Nitric Oxide Synthase and Cyclooxygenase in Macrophages, and Hydrogen Peroxide Generation in Mouse Skin, Biosci. Biotechnol. Biochem., vol. 64, No. 11, p. 2504-2507 (2000).
Kashman, Y., et al , "New Compounds from Avocado Pear," Tetrahedron, vol. 25, pp. 4617-4631, Pergamon Press, (1969).
Kabuki, T. et al., "Characterization of novel antimicrobial compounds from mango (*Mangifera indica* L.) kernel seeds," Food Chemistry, vol. 71, pp. 61-66, (2000).
Hashimura, H. et al., "Acetyl-CoA Carboxylase Inhibitors from Avocado (*Persea americana* Mill) Fruits," Biosci. Biotechnol. Biochem., vol. 65, No. 7, pp. 1656-1658 (2001).
Greene, T.W. et al., "Protective Groups in Organic Synthesis," Third Edition, Chapter 1: The Role of Protective Groups in Organic Synthesis, 16 pages (1999).
Foucault, A.P. et al., "Counter-current chromatography: instrumentation, solvent selection and some recent applications to natural product purification," Journal of Chromatography A., vol. 808, pp. 3-22 (1998).
Domergue, F. et al , "Antifungal compounds from idioblast cells isolated from avocado fruits," Phytochemistry, vol. 54, pp. 183-189 (2000).
Chia, T.W.R. et al., "Antimicrobial activity of crude epicarp and seed extracts from mature avocado fruit (*Persea americana*) of three cultivars," Pharmaceutical Biology, vol. 48, No. 7, pp. 753-756 (2010).
Chang, C-F, et al., "Isolation and Structure Elucidation of Growth Inhibitors for Silk-worm Larvae from Avocado Leaves," Short Communication: Agr. Biol. Chem., vol. 38, No. 5, pp. 1167-1168 (1975).
Canadian Food Directorate, Clostridium botulinum Challenge Testing of Ready-to-Eat Foods, Food Directorate, Health Products and Food Branch. Health Canada, Version No. 1, Issue Date. Nov. 24, 2010, 11 pages.
Butt, A.J. et al., "A novel plant toxin, persin, with in vivo activity in the mammary gland, induces Bim-dependent apoptosis in human breast cancer cells," Molecular Cancer Therapeutics, vol. 5, pp. 2300-2309 (2006).
Bull, S.D. et al., "Synthesis of the Avocado Antifungal, (Z,Z)-2-Hydroxy-4-oxohenicosa-12,15-dien-1-yl Acetate," Aust. J Chem , vol. 47, pp. 1661-1672 (1994).
Brown, B.I., "Isolation of Unpleasant Flavor Compounds in the Avocado (*Persea americana*)," J. Agr. Food Chem., vol. 20, No. 4, 5 pages (1972).
AOAC Official Method 966.04, Sporicidal Activity of Disinfectants, First Action 1966, Final Action 1967, Revised 2002, 6 pages.
Tang. Y., et al , "Inhibition of Food-Borne Pathogens by T1, a Novel Antimicrobial Peptide as a Potential Food Preservative," USDA National Agricultural Library, International Journal of Food Engineering, vol. 4, No. 4, 2008, (Abstract provided).
First Office Action for China Patent Application No. 201180048894.6 dated Jun. 11, 2014.
Second Office Action for China Patent Application No. 201180048894.6 dated Mar. 13, 2015.
Third Office Action for China Patent Application No. 201180048894.6 dated Oct. 26, 2015.
Notice of Reasons for Rejection for Japanese Patent Application 2013-523692 dated Aug. 24, 2015.
Extended European Search Report for European Patent Application No. 11828227.6 dated Dec. 11, 2013.
Partial European Search Report for European Patent Application No. 14176098.3 dated Feb. 2, 2015.
Idris et al., "Preliminary Phytochemical Screening and Antimicrobial Activity of Seed Extracts of *Persea Americana* (Avocado Pear)," Bayero Journal of Pure and Applied Sciences 2(1):173-176 (2009).
Extended European Search Report for European Patent Application No. 14176098.3 dated May 29, 2015.
Rodriguez-Saona et al., "Biologically Active Aliphatic Acetogenins from Specialized Idioblast Oil Cells," Current Organic Chemistry 4:1249-1260 (2000).
Rodriguez-Saona et al., "Isolation, Identification, and Biological Activity of Isopersin, a New Compound from Avocado Idioblast Oil Cells," J. Nat. Prod. 61:1168-1170 (1998).
Nagaraj et al., "Antioxidant and Antibacterial Activity of Avocado (*Persea gratissima* Gaertner) Seed Extract," World Applied Sciences Journal 9(6):695-698 (2010).

(56) References Cited

OTHER PUBLICATIONS

Fourth Office Action for China Patent Application No. 201180048894.6 dated Apr. 18, 2016.
Valeri et al., "Phytochemical and Toxicological Study of Pericarp of the Avocado Pear," Rev. Med. Vet. Parasitol (Maracay) vol. 13, pp. 37-58 (1954).
International Preliminary Report on Patentability and Written Opinion for corresponding International Application No. PCT/IB2011/053535 (dated Feb. 12, 2013).
International Search Report and Written Opinion for corresponding International Application No. PCT/IB2011/053535 (dated Aug. 3, 2012).
Office Action for U.S. Appl. No. 13/763,262 dated Jan. 6, 2016.

\* cited by examiner

ACETOGENIN MOLECULES HAVING ANTIPLATELET AND/OR ANTITHROMBIC ACTIVITIES, AND METHODS AND COMPOSITIONS THEREOF

FIELD OF THE DISCLOSURE

The present disclosure relates, in some embodiments, to molecules (e.g., acetogenin molecules) that may have antiplatelet and/or antithrombic activities. According to some embodiments, the present disclosure relates to pharmaceutical compositions comprising molecules (e.g., acetogenin molecules) that may have antiplatelet and/or antithrombic activities.

BACKGROUND OF THE DISCLOSURE

Platelets play a pivotal role in physiological hemostasis. However, in coronary arteries damaged by atherosclerosis, enhanced platelet aggregation, with subsequent thrombus formation, is a precipitating factor in acute ischemic events. Hence, pharmacological agents with antiplatelet actions are considered to be fundamental therapies in the prevention of atherothrombotic events.

Platelets normally circulate in a resting state and upon vascular injury they interact with components of the sub-endothelial matrix, particularly collagen and von Willebrand factor (vWF), via their respective receptors glycoprotein (GP) VI and GPIbN/IX. Agonists, such as collagen, ADP, arachidonic acid, epinephrine, thromboxane A2 (arachidonic acid-derived), and thrombin, are then released or produced to further amplify platelet activation by interacting with their respective membrane receptors. Hence, more circulating platelets from the blood flow are recruited to sustain hemostatic plug growth. The final pathway for all agonists is the activation of the platelet membrane GPIIb/IIIa integrin, leading to thrombus formation through fibrinogen bridges.

The most common antiplatelet agents currently used in clinical practice for the prevention of atherothrombosis are aspirin and clopidogrel. Their mechanisms of action are focused on inhibiting irreversibly amplification mechanisms of platelet activation by blocking the interaction of an agonist with its specific cell surface receptor. For instance, aspirin, as an irreversible inhibitor of cyclooxygenase (COX)-1, prevents arachidonic acid from being metabolized to prostaglandins G2/H2 and subsequently inhibits thromboxane A2 formation. Similarly, clopidogrel directly interferes with ADP binding to its P2Y12 receptor. However, antiplatelet agents, such as aspirin, are often associated with an increased risk of bleeding and frequently require gastric protection medications.

SUMMARY

Accordingly, a need has arisen for improved molecules, compositions, and methods for the reduction of platelet aggregation and atherothrombotic events. The present disclosure relates, according to some embodiments, to molecules, compositions, and methods for reduction of platelet aggregation and atherothrombotic events.

The present disclosure provides for acetogenin molecules. An acetogenin molecule may be selected from the group comprising Acetogenin 1, Acetogenin 2, Acetogenin 3, Acetogenin 4, Acetogenin 5, Acetogenin 6, Acetogenin 7, Acetogenin 8, Acetogenin 9, Acetogenin 10, Acetogenin 11, Acetogenin 12, Acetogenin 13, and Acetogenin 14, and hydrates, dehydrates, acetoxylates, deacetoxylates, acid salts, base salts, stereoisomers, or derivatives thereof. An acetogenin molecule may have at least one of an antiplatelet activity and an antithrombic activity.

The present disclosure provides for pharmaceutical compositions. A pharmaceutical composition may comprise a pharmaceutically-effective amount of one or more acetogenin molecules, which may each be selected from the group consisting of: Acetogenin 1, Acetogenin 2, Acetogenin 3, Acetogenin 4, Acetogenin 5, Acetogenin b, Acetogenin 7, Acetogenin 8, Acetogenin 9, Acetogenin 10, Acetogenin 11, Acetogenin 12, Acetogenin 13, and Acetogenin 14. A pharmaceutical composition may further comprise a pharmaceutically-acceptable agent.

One or more acetogenin molecules may comprise a first acetogenin molecule and a second acetogenin molecule, wherein a first acetogenin molecule and a second acetogenin molecule may be different. A pharmaceutically acceptable agent may comprise a carrier, an excipient, an enhancer, a solvent, a diluent, an adjuvant, an additive or any combination thereof. A solvent may be selected from the group consisting of water, ethanol, propylene glycol, polyethylene glycol, dimethyl sulfoxide, and combinations thereof.

A pharmaceutical composition may further comprise a salt, a buffer, a sugar, an amino acid, and combinations thereof. A pharmaceutical composition may further comprise sodium chloride, potassium chloride, sodium phosphate, potassium phosphate, dextrose, glycine, and combinations thereof. A pharmaceutical composition may be configured in a dosage form selected from the group consisting of a tablet, a pill, a granule, a powder, a cachet, a solution, a suspension, an emulsion, a syrup, an aerosol, a gelatin capsule, and a sterilized powder.

The present disclosure provides for methods of treating a subject. A method may comprise administering to a subject a pharmaceutically-effective amount of a pharmaceutical composition. A pharmaceutical composition may comprise one or more acetogenin molecules, wherein each of one or more acetogenin molecules may be selected from the group consisting of: Acetogenin 1, Acetogenin 2, Acetogenin 3, Acetogenin 4, Acetogenin 5, Acetogenin 6, Acetogenin 7, Acetogenin 8, Acetogenin 9, Acetogenin 10, Acetogenin 11, Acetogenin 12, Acetogenin 13, and Acetogenin 14. A pharmaceutical composition may further comprise a pharmaceutically-acceptable agent, wherein a pharmaceutically-effective amount may be sufficient to have an antiplatelet effect, an antithrombic effect, or combinations of an antiplatelet effect and an antithrombic effect.

One or more acetogenin molecules may comprise a first acetogenin molecule and a second acetogenin molecule, wherein a first acetogenin molecule and a second acetogenin molecule are different. A pharmaceutically acceptable agent may comprise a carrier, an excipient, an enhancer, a solvent, a diluent, an adjuvant, an additive or any combination thereof. A solvent may be selected from the group consisting of water, ethanol, propylene glycol, polyethylene glycol, dimethyl sulfoxide, and combinations thereof.

Pharmaceutical compositions according to the present disclosure may comprise a salt, a buffer, a sugar, an amino acid, and combinations thereof. Pharmaceutical compositions according to the present disclosure may comprise sodium chloride, potassium chloride, sodium phosphate, potassium phosphate, dextrose, glycine, and combinations thereof.

Pharmaceutical compositions may be configured in a dosage form selected from the group consisting of a tablet, a pill, a granule, a powder, a cachet, a solution, a suspension, an emulsion, a syrup, an aerosol, a gelatin capsule, and a powder. One or more acetogenin molecules may comprise a first acetogenin molecule, a second acetogenin molecule, and a third acetogenin molecule, wherein a first acetogenin molecule, a second acetogenin molecule, and a third acetogenin molecule may each be different.

The present disclosure provides for methods of formulating a pharmaceutical composition having antiplatelet and/or antithrombic activity. Methods of formulating a pharmaceutical composition having antiplatelet and/or antithrombic activity may comprise combining a pharmaceutically effective amount of one or more acetogenin molecules with a pharmaceutically acceptable solvent to form a pharmaceutical composition.

A pharmaceutically acceptable solvent may comprise water, a non-aqueous solvent, a combination of water and a non-aqueous solvent. In some methods, combining of one or more acetogenin molecules and a pharmaceutically acceptable solvent may further comprise wetting one or more acetogenin molecules with a pharmaceutically acceptable solvent, dispersing one or more acetogenin molecules in a pharmaceutically acceptable solvent, dissolving one or more acetogenin molecules in a pharmaceutically acceptable solvent, mixing one or more acetogenin molecules with a pharmaceutically acceptable solvent, or contacting one or more acetogenin molecules with a pharmaceutically acceptable solvent.

Methods of formulating a pharmaceutical composition having antiplatelet and/or antithrombic activity may further comprise combining a pharmaceutically acceptable agent with a pharmaceutically effective amount of one or more acetogenin molecules, with a pharmaceutically acceptable solvent, or with both a pharmaceutically effective amount of one or more acetogenin molecules and a pharmaceutically acceptable solvent.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

Some embodiments of the disclosure may be understood by referring, in part, to the present disclosure and the accompanying drawings, wherein.

DETAILED DESCRIPTION

Figure 1:
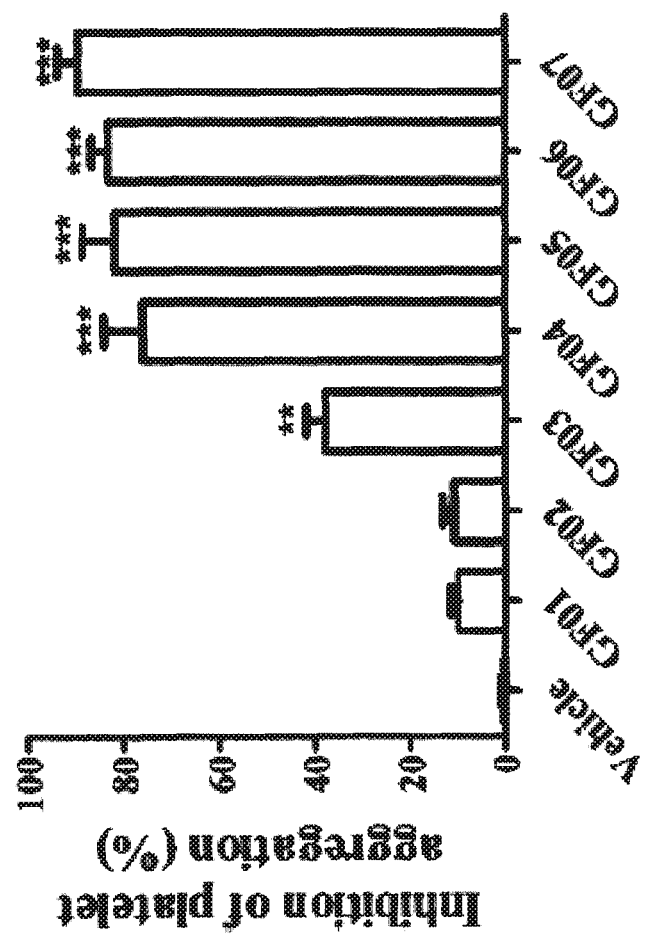
FIG. 1 is a graph illustrating the ADP-induced platelet aggregation inhibitory properties of subfractions GF01 to GF07, according to a specific example embodiment of the disclosure.

The present disclosure relates, in some embodiments, to molecules that may exhibit antiplatelet and/or antithrombic activities. According to some embodiments, the present disclosure relates to acetogenin molecules (e.g., acetoxylated, deacetoxylated) that may have antiplatelet and/or antithrombic activities. In some embodiments, the present disclosure relates to pharmaceutical compositions comprising acetogenin molecules that may have antiplatelet and/or antithrombic activities. The present disclosure, in some embodiments, further relates to methods of isolating acetogenin molecules (e.g., acetoxylated, deacetoxylated) that may have antiplatelet and/or antithrombic activities.

The present disclosure, in some embodiments, relates to molecules isolated from avocado (*Persea americana*) seed and pulp that may exhibit antiplatelet and/or antithrombic activities. However, a person having ordinary skill in the art would understand that the disclosed molecules may also be isolated from other organisms (e.g., *Persea* spp.) without departing from the scope of the present invention. Likewise, a person having ordinary skill in the art would understand that such molecules may be artificially generated using biotechnology techniques without departing from the scope of the disclosure.

Acetogenin Molecules

According to some embodiments, the present disclosure relates to acetogenin molecules (e.g., acetoxylated, deacetoxylated) that may exhibit at least one of an antiplatelet activity and an antithrombic activity. Antiplatelet activity may be assessed using one or more in vitro (e.g., platelet aggregation) and/or in vivo (e.g., blood clotting time) assays. Antiplatelet activity may be assessed, for example, using a light transmittance aggregometry test based on the stimulation of platelet-platelet aggregation in platelet-rich plasma after stimulation with various agonists (e.g., ADP, α Arachidonic acid, collagen etc). This test has been the most widely used technique to monitor the effects of antiplatelet agents. Agonists and their concentration may be used to produce full aggregation. Under this condition, acetogenins may inhibit aggregation induced by any agonist; their half maximal inhibitory concentration (IC50) value may vary by the agonist used. Percent aggregation inhibition values may be calculated using the following equation: % Inhibition= (Maximal aggregation vehicle control−Maximal aggregation acetogenins)/Maximal aggregation vehicle control× 100%. Under a dose-dependent antiplatelet activity, $IC_{50}$ may represent the concentration of acetogenins required for 50% inhibition of stimulation of platelet aggregation.

Antithrombic activity may be assessed using one or more in vivo (e.g., experimental thrombosis model) assays. For example, after thrombus induction, femoral segments may be removed, fixed, and stained. These segments may be then scored by a pathologist in a double blind manner. Quantitative measurement may be obtained by computerized plannimetry, reaching a quantitative morphological description of structures at the two-dimensional level. Image analysis may be performed using ImageJ software. Minimal occlusion (0.2%) may be observed in controls arteries and test specimens may display thrombus occlusion 40% of the vascular light.

In some embodiments, an acetogenin molecule may comprise 1-acetoxy-2,4-dihydroxy-n-heptadeca-16-ene (Acetogenin 1), having the structure:

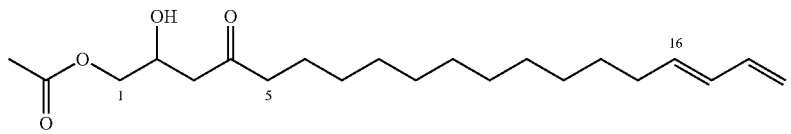 [SMILES: C=C/C=C/CCCCCCCCCCCC(=O)CC(O)COC(C)=O]

and/or hydrates, dehydrates, acetoxylates, deacetoxylates, acid salts, base salts, stereoisomers, or derivatives thereof.

According to some embodiments, an acetogenin molecule may comprise Persediene (Acetogenin 2), having the structure:

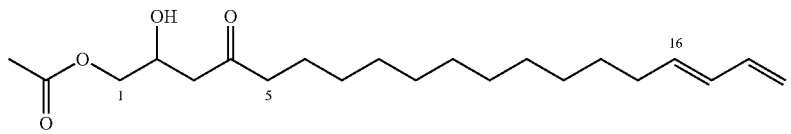 [SMILES: C=C/C=C/CCCCCCCCCCCC(=O)CC(O)COC(C)=O]

and/or hydrates, dehydrates, acetoxylates, deacetoxylates, acid salts, base salts, stereoisomers, or derivatives thereof.

An acetogenin molecule, in some embodiments, may comprise Persenone-C (Acetogenin 3), having the structure:

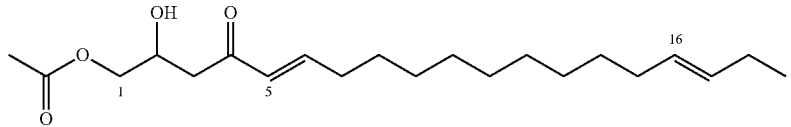 [SMILES: CC/C=C/CCCCCCCCC/C=C/C(=O)CC(O)COC(C)=O]

and/or hydrates, dehydrates, acetoxylates, deacetoxylates, acid salts, base salts, stereoisomers, or derivatives thereof.

In some embodiments, an acetogenin molecule may comprise Persenone-A (Acetogenin 4), having the structure:

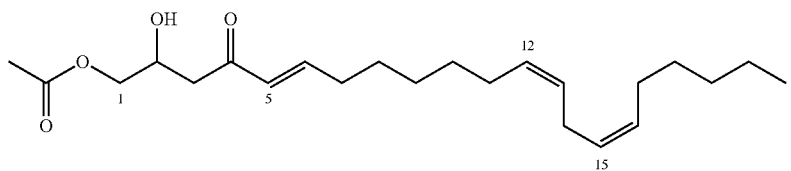

and/or hydrates, dehydrates, acetoxylates, deacetoxylates, acid salts, base salts, stereoisomers, or derivatives thereof.

In some embodiments, an acetogenin molecule may comprise Persenone-B (Acetogenin 5), having the structure:

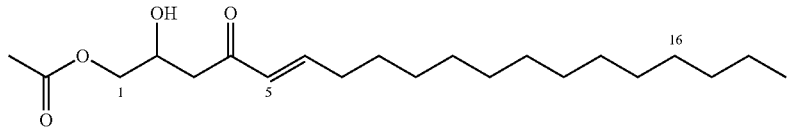 [SMILES: CCCCCCCCCCCCC/C=C/C(=O)CC(O)COC(C)=O]

and/or hydrates, dehydrates, acetoxylates, deacetoxylates, acid salts, base salts, stereoisomers, or derivatives thereof.

According to some embodiments, an acetogenin molecule may comprise Persin (Acetogenin 6), having the structure:

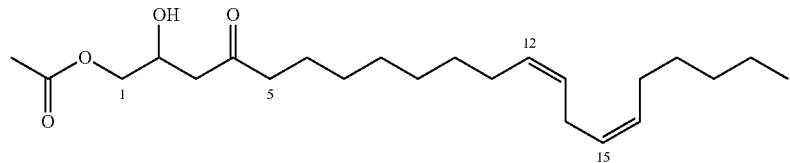 [SMILES: CCCCC/C=C\C/C=C\CCCCCCCC(=O)CC(O)COC(C)=O]

and/or hydrates, dehydrates, acetoxylates, deacetoxylates, acid salts, base salts, stereoisomers, or derivatives thereof.

An acetogenin molecule, in some embodiments, may comprise 1-acetoxy-2,4-dihydroxyheneicosa-12,15-diene (Acetogenin 7), having the structure:

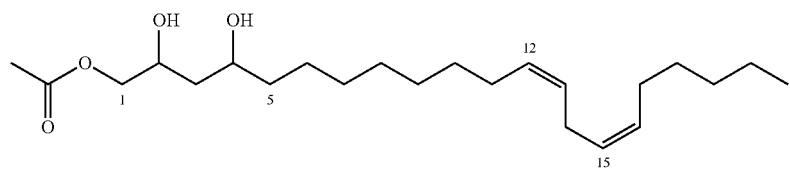 [SMILES: CCCCC/C=C\C/C=C\CCCCCCCC(O)CC(O)COC(C)=O]

and/or hydrates, dehydrates, acetoxylates, deacetoxylates, acid salts, base salts, stereoisomers, or derivatives thereof.

According to some embodiments, an acetogenin molecule may comprise AcO avocadenyne (Acetogenin 8), having the structure:

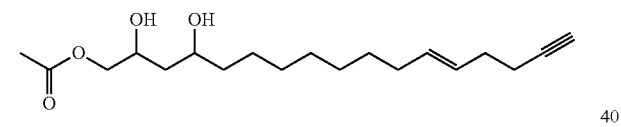

and/or hydrates, dehydrates, acetoxylates, deacetoxylates, acid salts, base salts, stereoisomers, or derivatives thereof.

In some embodiments, an acetogenin molecule may comprise AcO-avocadene (Acetogenin 9), having the structure:

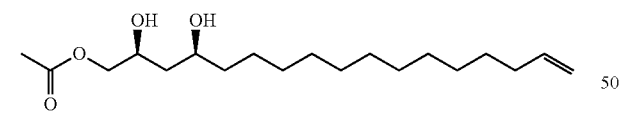

and/or hydrates, dehydrates, acetoxylates, deacetoxylates, acid salts, base salts, stereoisomers, or derivatives thereof.

In some embodiments, an acetogenin molecule may comprise Persediene (Acetogenin 10), having the structure:

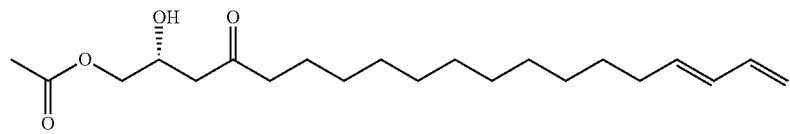 [SMILES: C=C/C=C/CCCCCCCCCCCC(=O)C[C@@H](O)COC(C)=O]

and/or hydrates, dehydrates, acetoxylates, deacetoxylates, acid salts, base salts, stereoisomers, or derivatives thereof.

An acetogenin molecule, in some embodiments, may comprise Persenone-C (Acetogenin 11), having the structure:

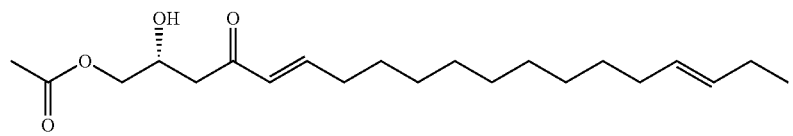 [SMILES: CC/C=C/CCCCCCCCC/C=C/C(=O)C[C@@H](O)COC(C)=O]

and/or hydrates, dehydrates, acetoxylates, deacetoxylates, acid salts, base salts, stereoisomers, or derivatives thereof.

An acetogenin molecule, in some embodiments, may comprise Persenone-B (Acetogenin 12), having the structure:

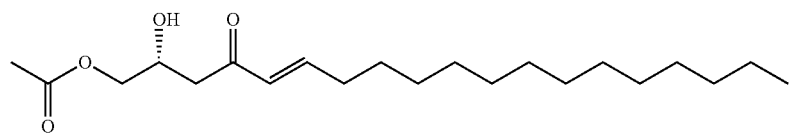 [SMILES: CCCCCCCCCCCCC/C=C/C(=O)C[C@@H](O)COC(C)=O]

and/or hydrates, dehydrates, acetoxylates, deacetoxylates, acid salts, base salts, stereoisomers, or derivatives thereof.

An acetogenin molecule, in some embodiments, may comprise Persenone-A (Acetogenin 13), having the structure:

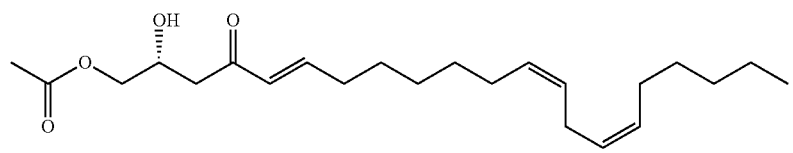 [SMILES: CCCCC/C=C\C/C=C\CCCCC/C=C/C(=O)C[C@@H](O)COC(C)=O]

and/or hydrates, dehydrates, acetoxylates, deacetoxylates, acid salts, base salts, stereoisomers, or derivatives thereof.

An acetogenin molecule, in some embodiments, may comprise Persin (Acetogenin 14), having the structure:

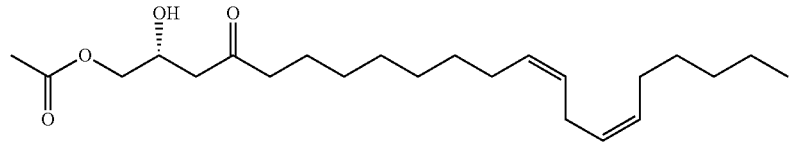 [SMILES: CCCCC/C=C\C/C=C\CCCCCCCC(=O)C[C@@H](O)COC(C)=O]

and/or hydrates, dehydrates, acetoxylates, deacetoxylates, acid salts, base salts, stereoisomers, or derivatives thereof.

According to some embodiments, an acetogenin molecule (e.g., acetoxylated, deacetoxylated) may be selected from the group comprising: Acetogenin 1, Acetogenin 2, Acetogenin 3, Acetogenin 4, Acetogenin 5, Acetogenin 6, Acetogenin 7, Acetogenin 8, Acetogenin 9, Acetogenin 10, Acetogenin 11, Acetogenin 12, Acetogenin 13, and Acetogenin 14.

Pharmaceutical Compositions

The present disclosure relates to pharmaceutical compositions comprising one or more acetogenin molecules that each may exhibit at least one of an antiplatelet activity and/or an antithrombic activity. An antiplatelet activity may be assessed using one or more in vitro (e.g., platelet aggregation) and/or in vivo (e.g., blood clotting time) assays. An antithrombic activity may be assessed using one or more in vivo (e.g., experimental thrombosis model) assays. Accordingly, by receiving one or more acetogenin molecules (e.g., in a biologically acceptable vehicle) a patient may have a decreased risk of an acute ischemic event. A pharmaceutical composition may be received by a subject by any appropriate or desired route. For example, a pharmaceutical composition may be received orally, parenterally, buccally, intraarterially, intracardially, intravenously, intraparietally, intrapulmonarily, sublingually, topically, transdermally, intranasally, intraarticular, intraosseously, and/or by combinations thereof.

Each acetogenin molecule may be selected from the group comprising: Acetogenin 1, Acetogenin 2, Acetogenin 3, Acetogenin 4, Acetogenin 5, Acetogenin 6, Acetogenin 7, Acetogenin 8, Acetogenin 9, Acetogenin 10, Acetogenin 11, Acetogenin 12, Acetogenin 13, and Acetogenin 14 and/or hydrates, dehydrates, acetoxylates, deacetoxylates, acid salts, base salts, stereoisomers, or derivatives thereof.

According to some embodiments, each acetogenin molecule (e.g., acetoxylated, deacetoxylated) may be included in a pharmaceutical composition at any desired concentration. For example, each acetogenin molecule (or the total of all acetogenins present) may be included in a pharmaceutical composition in an amount of about 0.15 mM, or about 0.2 mM, or about 0.3 mM, or about 0.4 mM, or about 0.5 mM, or about 1 mM, or about 2 mM, or about 5 mM, or about 10 mM, or about 15 mM. Each acetogenin molecule (e.g., acetoxylated, deacetoxylated) included in a pharmaceutical composition may be different and may be included at the same or different concentration than any other acetogenin(s)

present. For example, a pharmaceutical composition may comprise a first acetogenin molecule at a first concentration and a second acetogenin molecule at a second concentration, with the first concentration and the second concentration being the same or different. A pharmaceutical composition may comprise a first acetogenin molecule at a first concentration, a second acetogenin molecule at a second concentration, and a third acetogenin molecule at a third concentration with the first, second, and third concentrations being the same or different.

According to some embodiments, a (e.g., a pharmaceutical composition) may comprise, one or more acetogenins (e.g., acetoxylated, deacetoxylated), each present or all, when considered in total, present in a pharmaceutically effective amount, and one or more pharmaceutically acceptable agents. A pharmaceutically acceptable agent may enhance solubility (e.g., during formulation, in vivo, and/or in a final product), stability (e.g., during formulation, in vivo, and/or in a final product), delivery (e.g., viscosity, palatability), bioabsorption, bioavailability, and/or combinations thereof. In some embodiments, a composition (e.g., pharmaceutical composition) may comprise any desired carrier, excipient, enhancer, solvent, diluent, adjuvant, or other additive. A composition (e.g., pharmaceutical composition) may be configured as any desired delivery faun including, for example, tablet, pill, granule, powder, cachet, solution, suspension, emulsion, liquid (e.g., sterilized liquid for injection), syrup, aerosol, soft or hard, gelatin capsule, sterilized powder and the like. In some embodiments, a delivery vehicle may include a biologically acceptable molecule or composition.

Methods of Isolating an Acetogenin

The present disclosure further relates to methods of isolating and purifying an acetogenin (e.g., acetoxylated, deacetoxylated). According to some embodiments, a method may comprise lyophilizing avocado pulp to form a lyophilized avocado pulp, extracting a lyophilized avocado pulp with a first solvent (e.g., acetone) to form a solvent extracted pulp, fractionating a solvent extracted pulp by centrifuge partition chromatography to form one or more CPC fractions, and/or combinations thereof. A method may comprise, in some embodiments, separating (e.g., manually separating) avocado pulp from seeds to form a separated pulp mass, pureeing a separated pulp mass to form a pureed mass, vacuum packing a pureed mass to form a packed mass, and/or deep freezing (e.g., to or below about 70° C., to below −80° C.) a packed mass. According to some embodiments, centrifuge partition chromatography may comprise (a) contacting a solvent extracted pulp with a first CPC solvent system, to fond a first CPC solvent system mixture, (b) holding a first CPC solvent system mixture under conditions that permit separation into a first upper phase and a first lower phase, (c) contacting the first upper phase with a second CPC solvent system to form a second CPC solvent system mixture, (d) holding a second CPC solvent system mixture under conditions that permit separation into a second upper phase and a second lower phase, (e) contacting the first lower phase with a third CPC solvent system to form a third CPC solvent system mixture, (f) holding a third CPC solvent system mixture under conditions that permit separation into a third upper phase and a third lower phase, (g) combining the second upper phase or the second lower phase with the third upper phase or the third lower phase to form an acetogenin-enriched fraction, (h) contacting the acetogenin-enriched fraction with a fourth CPC solvent system to form a fourth CPC solvent system mixture, (i) holding a fourth CPC solvent system mixture under conditions that permit separation into a fourth upper phase and a fourth lower phase, and/or (j) fractionating the fourth lower phase by liquid chromatography (e.g., HPLC) to form at least one acetogenin fraction comprising at least one acetogenin molecule.

A first CPC solvent system, a second CPC solvent system, and a third CPC solvent system may each independently comprise two non-miscible solvents including, for example, a C1-C4 alcohol (e.g., methanol) and/or a C4-C10 alkane (e.g., heptane) in equal or approximately equal volumes. A first CPC solvent system, a second CPC solvent system, and a third CPC solvent system may be each independently prepared by saturating a C1-C4 alcohol (e.g., methanol) with a C4-C10 alkane (e.g., heptane) or saturating a C4-C10 alkane (e.g., heptane) with a C1-C4 alcohol (e.g., methanol). A fourth CPC solvent system may comprise, for example, heptane, ethyl acetate, methanol, and water (e.g., at a volume ratio of 8:2:8:2, respectively).

Methods of Formulation and Treatment

The present disclosure further relates to methods of formulating a pharmaceutical composition. According to some embodiments, a method of forming a liquid pharmaceutical compositions may comprise combining at least one acetogenin with water and/or another solvent to form solution. Combining at least one acetogenin with water may include wetting, dispersing, dissolving, mixing and/or otherwise contacting the at least one acetogenin with or in a solvent (e.g., an aqueous and/or non-aqueous solvent). In some embodiments, combining at least one acetogenin with water may include forming an homogenous oil in water mixture with or without an emulsifier and/or using any desired mixing system (e.g., microfluidization, fluidized bed). Examples of a solvent may include water, ethanol, propylene glycol, polyethylene glycol, dimethyl sulfoxide, and combinations thereof. Non-aqueous solvents, if included, may be combined with an acetogenin before addition of an aqueous solvent, if included. A pharmaceutically acceptable composition may include a salt (e.g., sodium chloride, potassium chloride), a buffer (e.g., sodium phosphate, potassium phosphate), a sugar (e.g., dextrose), an amino acid (e.g., glycine), and/or any other desired molecule, which, in each case, may be combined with acetogenin without, before, along with, and/or after combining with a solvent. A composition may include and/or be administered concurrently with fluids, nutrients (e.g., nutrient replenishers), chelating agents, antimicrobials, antioxidants, cyclodextrin, dextrin, and/or combinations thereof.

The present disclosure further relates to methods of treatment. According to some embodiments, a method of treatment may include providing a patient with a pharmaceutical composition, the pharmaceutical composition comprising at least one acetogenin molecule (e.g., acetoxylated, deacetoxylated) that may exhibit at least one of an antiplatelet activity and an antithrombic activity. The nature, number, and quantities of acetogenins to be administered to a subject may vary according to body mass of the subject, the desired anti-antiplatelet activity and/or anti-thrombic activity, the dosage form, the subject's risk of having a platelet-mediated adverse event (e.g., ischemic event) in the absence of treatment, presence or absence of any co-therapy, and the exigency of the circumstances, among other factors. In some embodiments, the combination of two or more acetogenin molecules may result in a greater combined anti-platelet activity when compared to the sum of the component acetogenins administered alone. In some embodiments, the dosage of each acetogenin and/or the total of all acetogenins may be about 1 µg/kg to about 250 mg/kg.

As will be understood by those skilled in the art who have the benefit of the instant disclosure, other equivalent or alternative molecules and compositions for a reduction of platelet aggregation and/or atherothrombotic events can be envisioned without departing from the description contained herein. Accordingly, the manner of carrying out the disclosure as shown and described is to be construed as illustrative only.

Persons skilled in the art may make various changes in the components of a pharmaceutical composition, routes of administration, and/or the individual steps of a method for isolating a described molecule without departing from the scope of the instant disclosure. For example, the nature, number, and/or quantity of acetogenins and/or pharmaceutically-acceptable agents may be varied. In addition, the dosage of a composition may be scaled up or down (e.g., by altering the quantity and/or concentration of an administered dosage form), to suit the needs and/or desires of a practitioner. Each disclosed method and method step may be performed in association with any other disclosed method or method step and in any order according to some embodiments. Where the verb "may" appears, it is intended to convey an optional and/or permissive condition, but its use is not intended to suggest any lack of operability unless otherwise indicated. Where open terms such as "including," "having" or "comprising" are used, one of ordinary skill in the art having the benefit of the instant disclosure will appreciate that the disclosed features or steps optionally may be combined with additional features or steps. Such option may not be exercised and, indeed, in some embodiments, disclosed systems, compositions, apparatuses, and/or methods may exclude any other features or steps beyond those disclosed herein. Elements, compositions, devices, systems, methods, and method steps not recited may be included or excluded as desired or required. Persons skilled in the art may make various changes in methods of preparing and using a composition, device, and/or system of the disclosure. For example, a composition, object, and/or system may be prepared and or used as appropriate for animal and/or human use (e.g., with regard to sanitary, infectivity, safety, toxicity, biometric, and other considerations).

Also, where ranges have been provided, the disclosed endpoints may be treated as exact and/or approximations as desired or demanded by the particular embodiment. Where the endpoints are approximate, the degree of flexibility may vary in proportion to the order of magnitude of the range. For example, on one hand, a range endpoint of about 50 in the context of a range of about 5 to about 50 may include 50.5, but not 52.5 or 55 and, on the other hand, a range endpoint of about 50 in the context of a range of about 0.5 to about 50 may include 55, but not 60 or 75. In addition, it may be desirable, in some embodiments, to mix and match range endpoints. Also, in some embodiments, each figure disclosed (e.g., in one or more of the examples, tables, and/or drawings) may form the basis of a range (e.g., depicted value+/−about 10%, depicted value+/−about 50%, depicted value+/−about 100%) and/or a range endpoint, With respect to the former, a value of 50 depicted in an example, table, and/or drawing may form the basis of a range of, for example, about 45 to about 55, about 25 to about 100, and/or about 0 to about 100. Disclosed percentages are weight percentages except where indicated otherwise.

All or a portion of composition and/or method for a reduction of platelet aggregation and/or atherothrombotic events may be configured and arranged to be disposable, serviceable, interchangeable, and/or replaceable. These equivalents and alternatives along with obvious changes and modifications are intended to be included within the scope of the present disclosure. Accordingly, the foregoing disclosure is intended to be illustrative, but not limiting, of the scope of the disclosure as illustrated by the appended claims.

The title, abstract, background, and headings are provided in compliance with regulations and/or for the convenience of the reader. They include no admissions as to the scope and content of prior art and no limitations applicable to all disclosed embodiments.

EXAMPLES

Some specific example embodiments of the disclosure may be illustrated by one or more of the examples provided herein.

Example 1: Preliminary Screening

Avocado pulp was manually separated from seeds, pureed, vacuum packed and stored at −80° C. prior to use, to avoid enzymatic activity. Avocado fruits (*Persea americana* Mill, cv. var. Hass) were obtained from the region of Uruapan, Mich., México (19°25'0"N 102°4'0"O).

An acetone extract E001 was obtained from freeze-dried avocado pulp, which was partitioned in a heptane-methanol biphasic system, and further fractionated by centrifuge partition chromatography (CPC). Fractions with similar HPLC-PDA chromatographic profiles (at 220 nm) were grouped together, as described in D. G. Rodriguez-Sanchez, C. Silva-Platas, R. P. Rojo, N. García, L. Cisneros-Zevallos, G. García-Rivas and C. Hernández-Brenes, Activity-guided identification of acetogenins as novel lipophilic antioxidants present in avocado pulp (*Persea americana*), *J. Chromatogr., B: Biomed. Appl.*, 2013, 942-943, 37-45. Grouping resulted in seven different avocado pulp subfractions, designated as GF01 to GF07.

Subfractions GF01 to GF07 were evaluated for ADP-induced platelet aggregation inhibitory properties. Calculated KD values ranged from 0.14-0.40, 0.83-1.13, 1.59-1.72, 2.03-2.41, 4.12-5.82, 7.37-11.67 and 14-∞, for fractions GF01 to GF07, respectively. Potential inhibitory effects on platelet aggregation, for fractions GF01 to GF07 (at 500 μg solid dry-weight (dw) $mL^{-1}$), were measured turbidimetrically on platelets induced by ADP. The percent inhibition of ADP-induced (20 μM) platelet aggregation exhibited by the groups of avocado pulp fractions GF01 to GF07 (500 μg solid dry weight mL−1), obtained after partition and centrifugal partition chromatography purification of acetone soluble solids from avocado pulp is illustrated in FIG. 1. As shown in FIG. 1, fractions GF03 to GF07 significantly inhibited (P<0.01) platelet aggregation in reference to the control, with P<0.01, *P<0.001 compared with the vehicle control (one-way ANOVA with Dunnett-corrected post hoc analyses). However, GF03 exhibited lower inhibition values (38±4.15%) than the rest of the fractions, which resulted in levels of over 75% inhibition.

In the presence of equal concentrations of solids from each fraction (500 μg solid dw $mL^{-1}$), platelet viability was found to be >80%, for fractions GF02 to GF07 (data not shown), suggesting that platelet integrity appeared to be not affected by compounds present in those fractions at concentrations evaluated in the platelet aggregation assay. However, compounds present in fraction GF01 appeared to have a negative effect on platelet function resulting in 62.5±9.68% viability. Based on the higher activity and minimal effects on platelet viability, GF04 to GF07 were further characterized to determine the nature of the phytochemicals therein contained.

Mass spectrometry analysis of chromatographic peaks that were contained in the four fractions (GF04 to GF07), which presented the highest platelet aggregation inhibitory effects, consistently presented a similar ion pattern of [M+Na]$^+$ and [M+H]$^+$ molecular ions. In addition, fragment ions showing successive losses of H2O and/or acetic acid ($C_2H_4O_2$) from the [M+H]$^+$ ion were also present. This pattern was in accordance with the characteristic ion pattern reported for acetogenins, and more specifically for acetylated acetogenins derived from avocado fruit. Chemical identities were assigned to the chromatographic peaks by comparison of their mass spectra with values reported in the literature, and with data from standards isolated in our laboratory from avocado seeds. As shown in Table 1, compounds were identified as: 1-acetoxy-2,4-dihydroxy-n-heptadeca-16-ene; Persediene; Persenone-C; Persenone-A; Persenone-B; Persin; and 1-acetoxy-2,4-dihydroxyheneicosa-12,15-diene. Data from the preliminary screening study suggest the inhibition of platelet aggregation in the presence of fractions containing acetogenins obtained from avocado pulp.

TABLE 1

Chemical identity of the common acetogenins present in the groups of fractions with the highest antiplatelet activity (GF04 to GF07)

| # | [M + H]$^+$ (m/z)$^a$ | Ions pattern (m/z)$^a$ | Structure and Compound |
|---|---|---|---|
| 1 | 329 | 351, 311, 269, 251 | 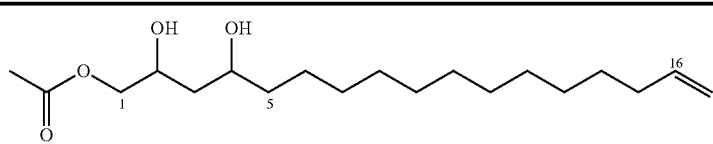 (2S,4S)-1-acetoxy-2,4-dihydroxy-n-heptadeca-16-ene (Acetogenin 1) |
| 2 | 353 | 375, 335, 293 | 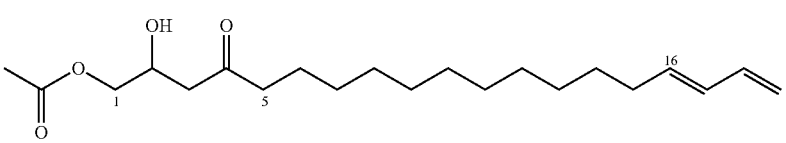 [SMILES: C=C/C=C/CCCCCCCCCCCC(=O)CC(O)COC(C)=O] Persediene (Acetogenin 2) |
| 3 | 353 | 375, 335, 293 | 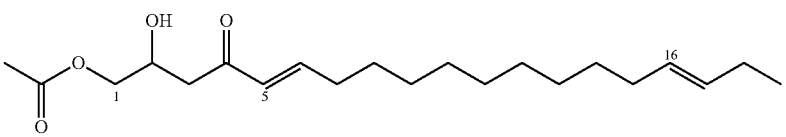 [SMILES: CC/C=C/CCCCCCCCC/C=C/C(=O)CC(O)COC(C)=O] Persenone-C (Acetogenin 3) |
| 4 | 379 | 401, 361, 319, 301 | 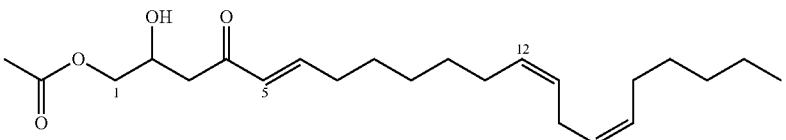 Persenon-A (Acetogenin 4) |
| 5 | 355 | 377, 337, 295 | 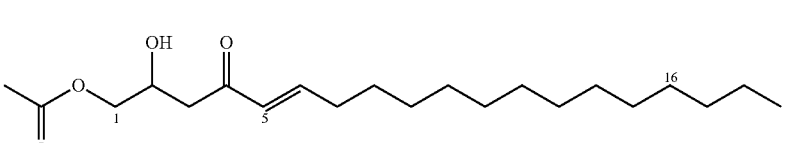 Persenone-B (Acetogenin 5) |
| 6 | 381 | 403, 363, 321, 303 | 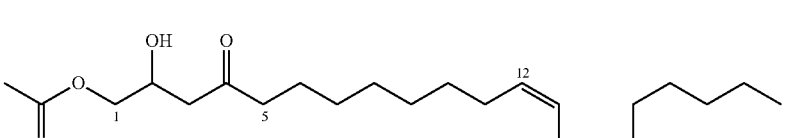 Persin (Acetogenin 6) |

TABLE 1-continued

Chemical identity of the common acetogenins present in the groups of
fractions with the highest antiplatelet activity (GF04 to GF07)

| # | [M + H]+ (m/z)[a] | Ions pattern (m/z)[a] | Structure and Compound |
|---|---|---|---|
| 7 | 383 | 365, 323, 305 | 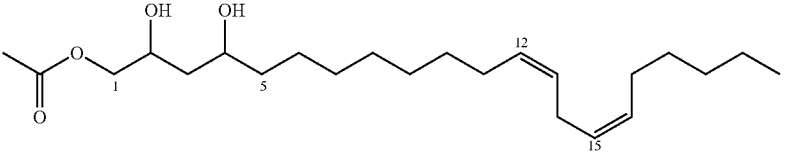 [SMILES: CCCCC/C=C\C/C=C\CCCCCCCC(O)CC(O)COC(C)=O]<br>(12Z, 15Z)-1-acetoxy-2,4-dihydroxyheneicosa-12,15-diene (Acetogenin 7) |

[a]MS/TOF detection using the electrospray ionization interface in positive-ion mode of analysis.

Chromatographic profiles and the identity of the compounds present in fractions with higher antiplatelet activity were obtained using the HPLC-PDA/TOF method described in Example 4.

Example 2: Large Scale Isolation and Purification of Active Constituents

Figure 2:
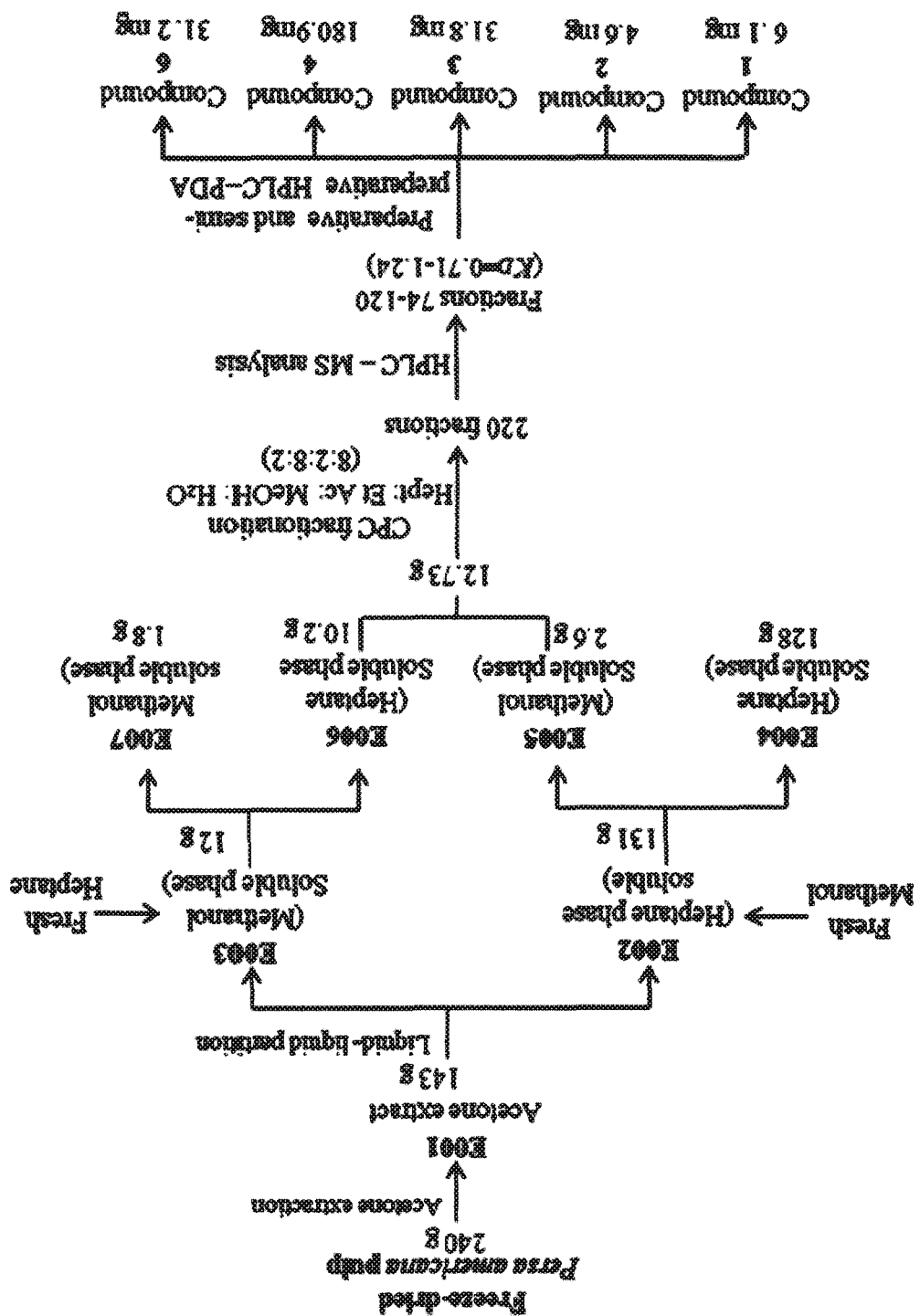
FIG. 2 illustrates a large scale isolation and purification process developed to recover compounds having potential antiplatelet activity from fractions with higher antiplatelet activity, according to a specific example embodiment of the disclosure.

As illustrated in FIG. 2, a large scale isolation and purification process was developed to recover the compounds having potential antiplatelet activity from fractions with higher antiplatelet activity. An acetone extract E001 from freeze-dried avocado pulp (240 g) was obtained and partitioned in a two non-miscible solvent system comprised of heptane-methanol (1:1 v/v), as described in D. G. Rodriguez-Sanchez, C. Silva-Platas, R. P. Rojo, N. García, L. Cisneros-Zevallos, G. García-Rivas and C. Hernández-Brenes, Activity-guided identification of acetogenins as novel lipophilic antioxidants present in avocado pulp (*Persea americana*), *J. Chromatogr., B: Biomed. Appl.*, 2013, 942-943, 37-45. Phase E002 (upper) and phase E003 (lower) were separated and washed with methanol saturated with heptane or heptane saturated with methanol (1:1 v/v), respectively. Phases were separated and concentrated under reduced pressure, yielding heptane- and methanol-soluble semicrude subfractions: E004 and E005 (derived from E002, respectively), and E006 and E007 (resulting from E003, respectively). Chromatographic profiles of sub-fractions E001 to E007 were obtained using the HPLC-PDA method further described in Example 4.

After HPLC-PDA evaluation, E005 and E006 sub-fractions were mixed and further fractionated in a 1 L CPC system (Kromaton Technologies, Angers, France) using heptane-ethyl acetate-methanol-water (8:2:8:2) as a solvent system. The upper phase (UP) of the solvent system served as the stationary phase (SP), and after hydrodynamic equilibrium establishment, the lower phase (LP) accounted for 18% of the total column volume. Extracts E005 and E006 (12.73±0.77 g), dissolved in 30 mL of UP and 80 mL of LP, were injected into the CPC column. LP was used to elute fractions for 170 min and then UP was pumped for 100 more minutes, both at a 10 mL min$^{-1}$ flow rate. A total of 240 fractions (10 mL per fraction) were collected and their corresponding partition coefficients (KD) were calculated as described by A. Berthod, J. B. Friesen, T. Inui and G. F. Pauli, Elution extrusion countercurrent chromatography: theory and concepts in metabolic analysis, *Anal. Chem.*, 2007, 79(9), 3371-3382. Aliquots (0.5 mL) of every 10 fractions were taken, evaporated under a stream of nitrogen and resuspended in isopropanol (0.5 mL) for further HPLC-PDA and HPLC-MS-TOF analysis as described in Example 4. At the end of the CPC run, the column was entirely filled with the SP, so it was ready to be reequilibrated again by pumping LP, and subsequent chromatographic fractionations were carried out.

Figure 3:
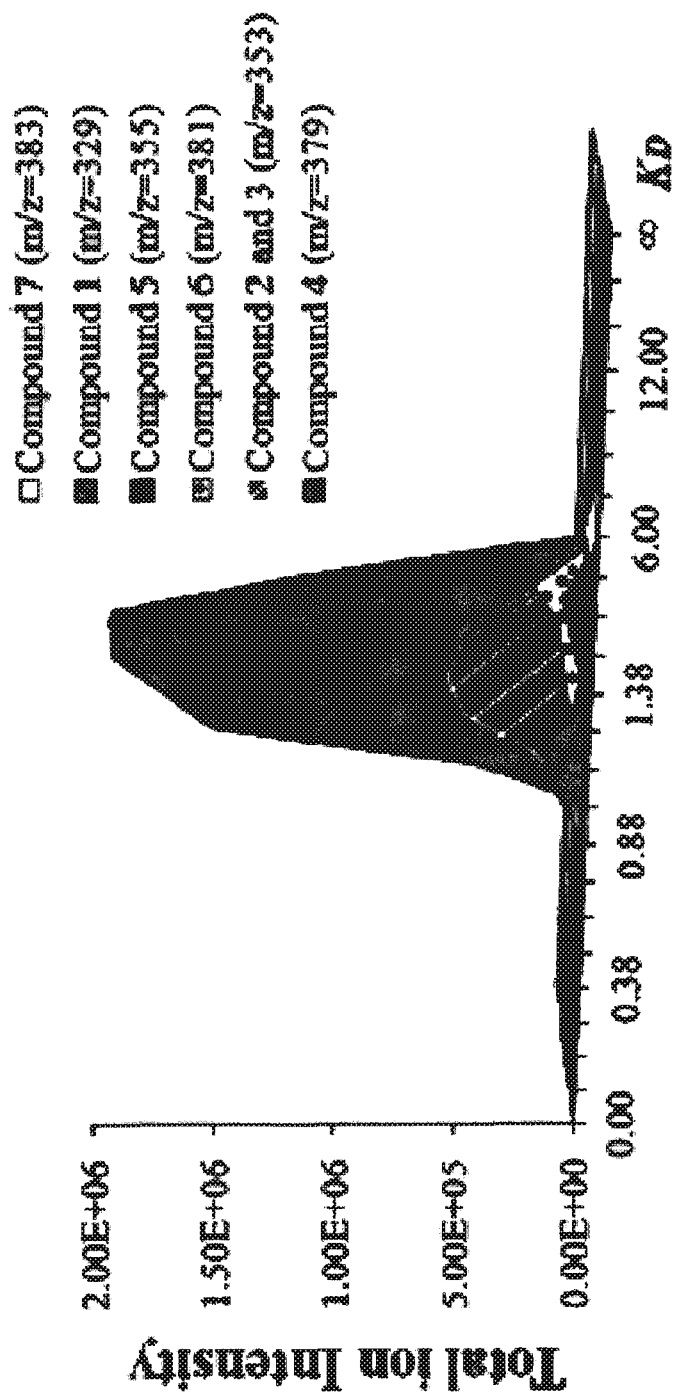
FIG. 3 is a graph illustrating the tracking of compounds 1 to 7 based on mass spectra from CPC fractions, according to a specific example embodiment of the disclosure.

Mass spectra from CPC fractions were obtained (every 10 fractions), and used as a tool to track the location of compounds 1 to 7 and selectively isolate them from the fractions in which they were preferably enriched. As shown in FIG. 3, the total ion intensity values were obtained by HPLC-MS analysis of different avocado pulp fractions isolated from an acetogenin-enriched extract. This data was used to track the location of the isolates and selectively isolate the compounds from the fractions in which they were preferably enriched. As shown in FIG. 3, KD values ranging from 0.90 to 1.52 corresponded to fractions 74-120. Based on their higher relative concentrations, compounds 1 to 4 and 6 were then selected for further purification by preparative and semi-preparative HPLC sequential runs.

Example 3: Acetogenin Purification

Consecutive HPLC separations were carried out in a preparative Phenomenex Prodigy C18 column (250×20 mm, 5 μm), using water 100% (A) and methanol 100% (B) as eluents, at a 20 mL min$^{-1}$ flow rate. The solvent gradient was: 0-4 min, 75-85% B linear; 4-22 min, 85% B isocratic; 22-24 min, 85-95% B linear; 24-32 min, 95% B isocratic. A photodiode (PDA) detector was set at 220 nm. The final purification was conducted in a semi-preparative Phenomenex Synergi Hydro-RP column (250×4.6 mm, 4 μm), using 100% water and 100% methanol as mobile phases (A and B, respectively) at a flow rate of 1 mL min$^{-1}$. Isocratic methods were optimized for each peak.

Example 4: Identification of Active Compounds

For chemical identity the compounds were subjected to HPLC-PDA and HPLC-MS analysis as previously described in D. G. Rodriguez-Sanchez, C. Silva-Platas, R. P, Rojo, N. García, L. Cisneros-Zevallos, G. García-Rivas and C. Hernández-Brenes, Activity-guided identification of acetogenins as novel lipophilic antioxidants present in avocado pulp (*Persea americana*), *J. Chromatogr., B: Biomed. Appl.*, 2013, 942-943, 37-45. Chemical identity was assigned by comparison of spectroscopic data with values reported in the literature and with data from standards isolated in our laboratory from avocado seeds.

Example 5: In Vitro Assays

To confirm the contribution of the isolated acetogenin compounds to antiplatelet activity, their individual activity was evaluated at different concentrations (0.15-15 mM). Aggregation was induced by different agonists that included collagen (5 μg mL−1), ADP (20 μM) and arachidonic acid (500 μM) in an approximation to explore the potential interference of acetogenins with the binding of a particular agonist to its cell surface receptor.

The platelet aggregation (induced by ADP, collagen and arachidonic acid) inhibitory activity of the purified molecules was evaluated was conducted in accordance with the Helsinki Declaration using human blood donated to the blood bank of Instituto Nacional de Cardiología Ignacio Chávez. Blood samples were taken from healthy volunteers who had not taken any medications for at least 2 weeks, or ingested any alcohol for at least 24 h prior to sample collection. Blood was collected by venipuncture into Vacutainer (BD Diagnostics, Plymouth, UK) tubes containing 3.8% sodium citrate as an anticoagulant (at a 9:1 ratio, v/v). Platelet-rich plasma (PRP) and platelet-poor plasma (PPP) were obtained as earlier reported by A. De la Peña, G. Baños, R. Izaguirre, J. J. Mandoki and J. M. Fernández, Comparative effect of synthetic aminoestrogens with estradiol on platelet aggregation, *Steroids,* 1993, 58(9), 407-409. The assays were carried out within 2 h after the blood had been drawn.

Evaluation of platelet aggregation was performed by turbidimetric measurements according to S. S. Falkenberg, I. Tarnow, A. Guzman, P. Molgaard and H. T. Simonsen, Mapuche herbal medicine inhibits blood platelet aggregation, *Evid. Based Complement. Alternat. Med.,* 2012, 2012, 647620, with some modifications. PRP adjusted with PPP to a platelet count of 2.5×108 mL$^{-1}$ (215 μL) was pre-incubated at 37° C. for 10 min with the evaluated sample (10 μL) and at various concentrations.

Platelet aggregation was initiated by the addition of 25 μL of the platelet agonist. The final concentrations of agonists in the reaction mixture were 20 μM ADP, 500 μM arachidonic acid or 5 μg mL$^{-1}$ collagen, all obtained from Chrono-PAR. Corporation (Havertown, Pa., USA). Aggregation response was recorded for 10 min using a Chrono-log Model 700 Whole Blood/Optical Lumi-Aggregometer (Chrono-Log, Havertown, Pa., USA). Maximal aggregation (MA) observed for samples containing avocado extracts, at different degrees of purification, was compared to those of vehicle controls (DMSO 2 M) evaluated under the same experimental conditions. Percent aggregation inhibitions, for all samples, were calculated using the following equation: % Inhibition=(MA vehicle control−MA extract)/MA vehicle control×100%.

To verify the possible platelet cytotoxic effects of avocado extracts at different degrees of purification, cell viability was measured using CellTiter-Blue (Promega, Madison, Wis., USA) and by trypan blue exclusion, counting live/dead platelets.

Statistically significant differences among groups were analyzed employing one-way analysis of variance (ANOVA), and differences between the control and the treated group were estimated by Dunnett's or LSMean Student's tests as appropriate. Differences were considered significant at a level of P<0.05. Half-maximal inhibitory concentrations (IC$_{50}$, μM) of platelet aggregation were determined by nonlinear regression analysis using a sigmoidal concentration-response equation. Statistical calculations were performed using the GraphPad Prism software, version 5.0 (GraphPad Software, San Diego, Calif., USA).

Table 2 provides the IC$_{50}$ values for the isolated acetogenin compounds as determined by platelet aggregation assays. The data are representative of at least three independent experiments. Results are expressed as means±SEM.

TABLE 2

Half-maximal inhibitory concentrations (IC$_{50}$) presented by purified acetogenins in a platelet aggregation assay, induced by different agonists

| Evaluated Sample | Half-maximal inhibition concentrations (IC$_{50}$ (mM))[a,b] | | |
|---|---|---|---|
| | Collagen (5 μg mL$^{-1}$) | ADP (20 μM) | Arachidonic acid (500 μM) |
| (2S,4S)-1-acetoxy-2,4-dihydroxy-n-heptadeca-16-ene (Acetogenin 1) | 8.18 ± 1.48bc[c] | 7.29 ± 1.21b | 13.42 ± 1.26c |
| Persediene (Acetogenin 2) | 11.99 ± 1.24c | >15 | >15 |
| Persenone-C (Acetogenin 3) | 5.23 ± 1.19b | 3.42 ± 1.56a | 7.40 ± 1.20b |
| Persenone-A (Acetogenin 4) | 8.73 ± 1.25bc | 13.48 ± 1.41c | >15 |
| Persin (Acetogenin 5) | >15 | >15 | >15 |
| Aspirin (acetylsalicylic acid) | 0.38 ± 0.07a | 3.65 ± 0.07a | 0.07 ± 0.01a |

[a]Values represent mean ± standard deviation (n = 4).
[b]">15" means that the achieved inhibition was lower than 50%, at 15 mM.
[c]Different letter in the same column indicate that values are significantly different (P < 0.05) by the LSMean Student's t-test.

As shown in Table 2, Persenone-C presented a significantly lower (P<0.05) IC$_{50}$ than the other compounds for collagen, ADP and arachidonic acid (3.42±1.56, 5.22±1.19, 7.40±1.20 mM, respectively). (2S, 4S)-1-acetoxy-2,4-dihydroxy-n-heptadeca-16-ene also inhibited platelet aggregation induced by all three agonists, but at >1.5-fold higher concentrations than Persenone-C. Whereas Persenone-A exhibited a similar IC$_{50}$ to (2S, 4S)-1-acetoxy-2,4-dihydroxy-n-heptadeca-16-ene against collagen-induced aggregation, but even at the highest concentrations (15 mM) tested it was unable to reach 50% inhibition when aggregation was induced by arachidonic acid. Isolated Persediene and Persin showed significantly lower platelet aggregation inhibition levels. Persediene inhibited collagen-induced aggregation; however, Persin did not inhibit platelet aggregation at any of the evaluated concentrations. Incubation of the platelets with purified compounds at 15 mM had no effect on the platelet viability (data not shown).

Persenone-C exhibited the most potent activity, as shown in Table 2. As expected, aspirin markedly inhibited ($IC_{50}$=0.07±0.01 μM) arachidonic acid-induced platelet aggregation with $IC_{50}$ values and 50-fold lower than that observed for collagen- and ADP-induced aggregation, respectively. In contrast, purified acetogenins did not exhibit such an evident selective inhibition for any of the evaluated agonists. This observation suggests that acetogenins do not interfere with the binding of the evaluated agonists to their specific receptors on the platelet's surface.

As described in Example 1, preliminary screening studies showed that fractions containing mixtures of compounds, evaluated at concentrations of 500 μg solid dw $mL^{-1}$, presented inhibitory concentrations of greater than 80% (FIG. 1). However, as shown in Table 2, purified compounds presented higher $IC_{50}$ values (3.42 mM=1207 μg $mL^{-1}$) than semi-pure fractions. This suggests that their may be synergistic interactions between compounds in mixture, including the acetogenin compounds.

Example 6: In Vivo Assays

One of the purified molecules exhibiting antiplatelet activity, Persenone-A, was selected for further evaluation of its performance as an antiplatelet agent in in vivo studies. Persenone-A was not the most potent antiplatelet acetogenin, but it was selected for in vivo evaluation because of its higher recovered yields.

All in vivo experiments were conducted in accordance with the Mexican National Protection Laws on Animal Protection and the General Health Law Related to Health Research (NOM-062-Z00-1999). All procedures were approved by an ethics committee. Male adult CD1 mice weighing 25-35 g were used (obtained from the Animal Care Unit from Facultad de Medicina, UNAM).

Animals were distributed among groups according to a balanced design based on body weight (3 animals per group in each experiment). Room temperature was kept constant (21-24° C.), and with light-dark cycles of 12 h. Food and water were given ad libitum. Persenone-A was dissolved in DMSO (vehicle) and administered intraperitoneally (i.p.). Control animals only received the vehicle (1.66 mL kg−1).

In a blood clotting time test groups of animals received a single i.p. administration of Persenone A (1, 10 or 100 mg $kg^{-1}$ of body weight, respectively) or vehicle. Blood clotting time was measured 24 h after administration, as described in R. Jaimez, A. Cooney, K. Jackson, A. E. Lemus, C. Lemini, M. Cárdenas, R. García, G. Silva and F. Larrea, In vivo estrogen bioactivities and in vitro estrogen receptor binding and transcriptional activities of anticoagulant synthetic 17betaaminoestrogens, *J. Steroid Biochem. Mol. Biol.*, 2000, 73(1-2), 59-66. The tail of the animal was warmed in a water bath at 37° C. for 3 min. The tail was dried and transected at 8 mm from the tip with a scalpel. Briefly, a 25 μL blood sample was collected from the bleeding tail tip into a microhematocrit glass capillary tube. The capillary tube was alternatively tilted to angles of +60° and −60° with respect to the horizontal plane, allowing blood to flow by gravity between two marks, separated by 45 mm. Time was counted from the instant that blood first made contact with the glass capillary tube and until the blood ceased to flow. The blood clotting time data were presented as the relative increase elicited by Persenone-A as a percentage of that obtained in samples treated with the vehicle.

Figure 4:
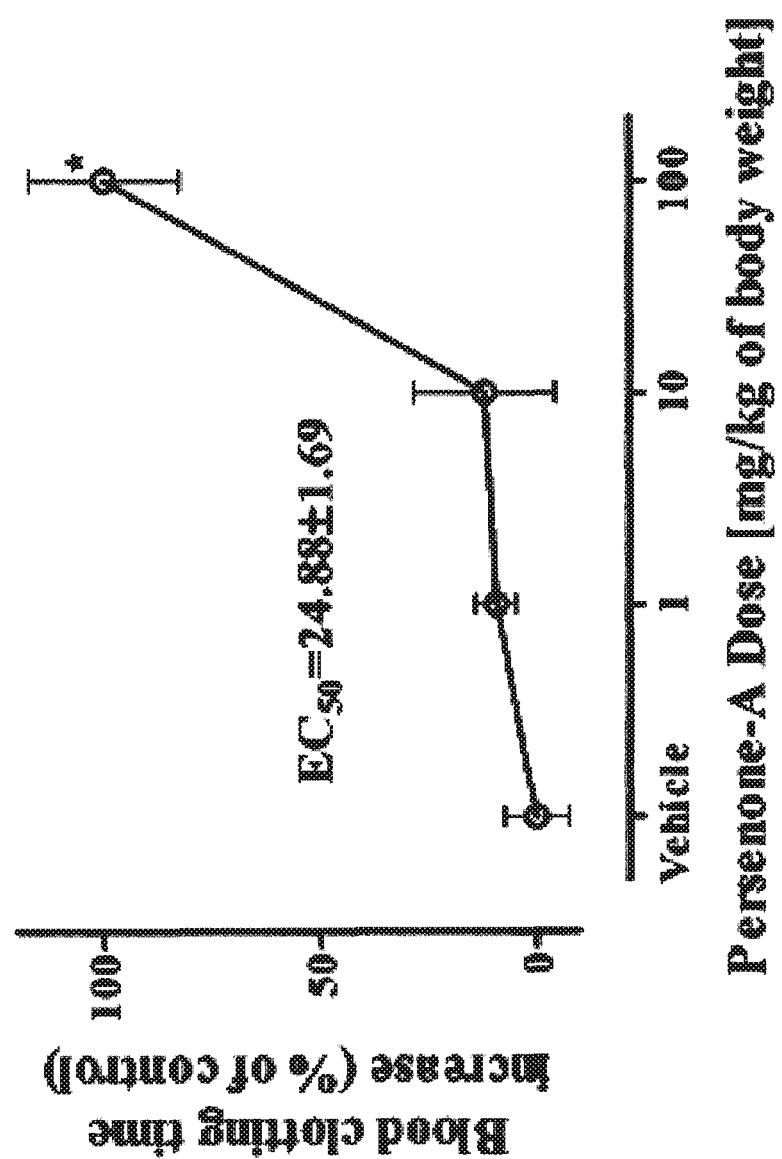
FIG. 4 is a graph showing the results of an in vivo analysis of blood clotting time for mice treated with Persenone-A (Acetogenin 4), according to a specific example embodiment of the disclosure.

As shown in FIG. 4, findings indicate that at 100 mg $kg^{-1}$, Persenone-A produced a 2-fold increase in blood clotting time. The calculated $EC_{50}$ value for Persenone-A was 24.8±1.7 mg $kg^{-1}$ of body weight (FIG. 4). Thus, it was confirmed that the antiplatelet activity of acetogenins initially observed in vitro was successfully reflected in in vivo models.

The data shown in FIG. 4 is representative of at least three independent experiments. Results were expressed as means±SEM. Statistically significant differences among groups were analyzed employing one-way analysis of variance (ANOVA), and differences between the control and the treated group were estimated by Dunnett's or LSMean Student's tests as appropriate. Differences were considered significant at a level of P<0.05. Half-maximal effective concentrations ($EC_{50}$, mg $kg^{-1}$ body weight) of blood clotting times were determined by nonlinear regression analysis using a sigmoidal concentration-response equation. Statistical calculations were performed using the GraphPad Prism software, version 5.0 (GraphPad Software, San Diego, Calif., USA).

Additionally, an experimental thrombosis model test was performed by subjecting mice to an acute ischemic challenge. Groups of animals received a single i.p. administration of Persenone-A (25 mg $kg^{-1}$ of body weight) or vehicle. After 24 h of treatment, mice were anesthetized with phenobarbital (80 mg $kg^{-1}$). Thrombosis was induced by a surgical model by tightening two sutures separated by 1 cm for 1 h to cause vascular occlusion in the right leg femoral vasculature. The vascular segments were then removed, fixed in formalin, dehydrated and embedded in paraffin. 4 μm thick sections were stained with Masson's trichrome and hematoxylin-eosin, and scored by a pathologist for the percentage of thrombus induction based on the occlusion of vascular light.

Figure 5A:
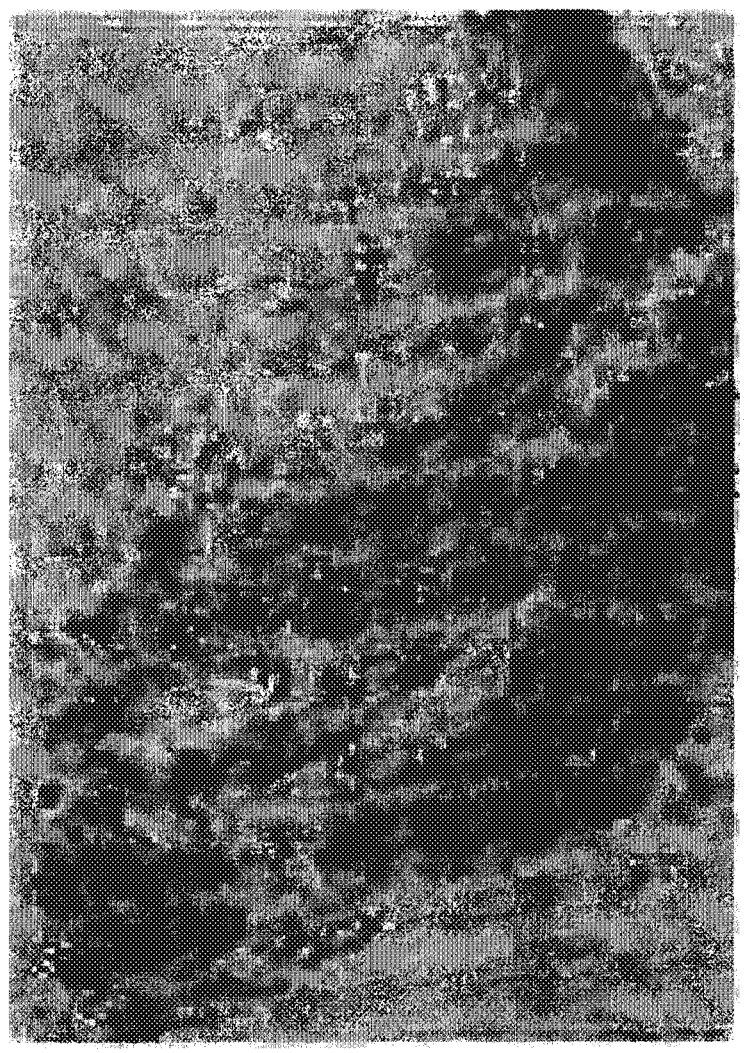
FIG. 5A shows a transverse section of the femoral vasculonervous package stained with Masson's trichome of a mouse femoral artery that does not present thrombi (control), according to a specific example embodiment of the disclosure.
Figure 5B:
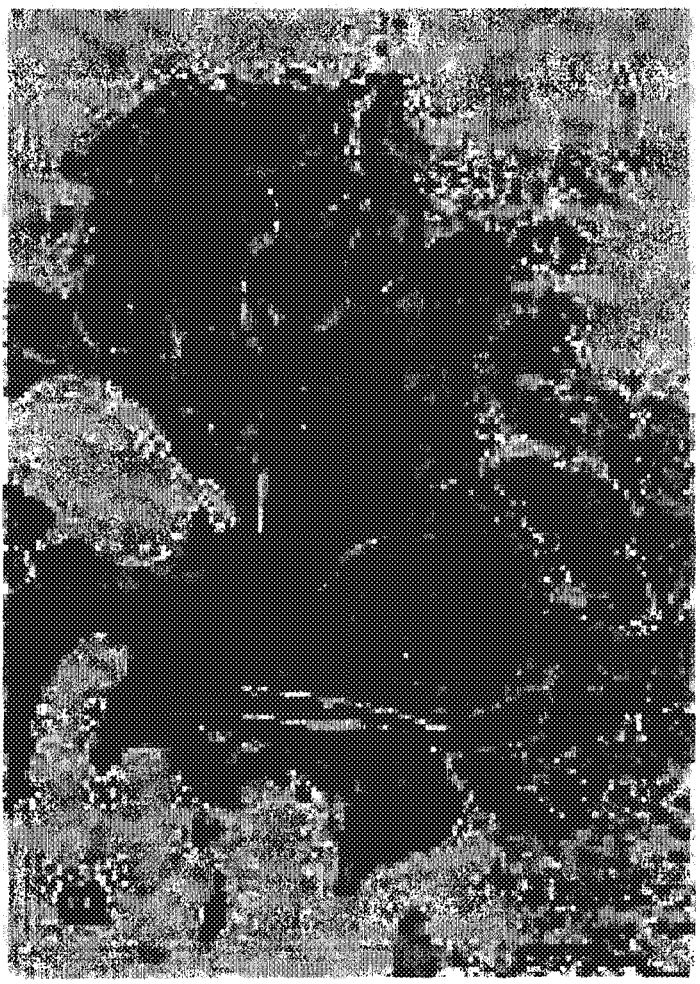
FIG. 5B shows a transverse section of the femoral vasculonervous package stained with Masson's trichome of a mouse femoral artery that has surgical induction of the thrombus (stasis), according to a specific example embodiment of the disclosure.
Figure 5C:
FIG. 5C shows a transverse section of the femoral vasculonervous package stained with Masson's trichome of a mouse femoral artery that has surgical induction of the thrombus (stasis) after treatment with Persenone-A (Acetogenin 4), according to a specific example embodiment of the disclosure.
Figure 5D:
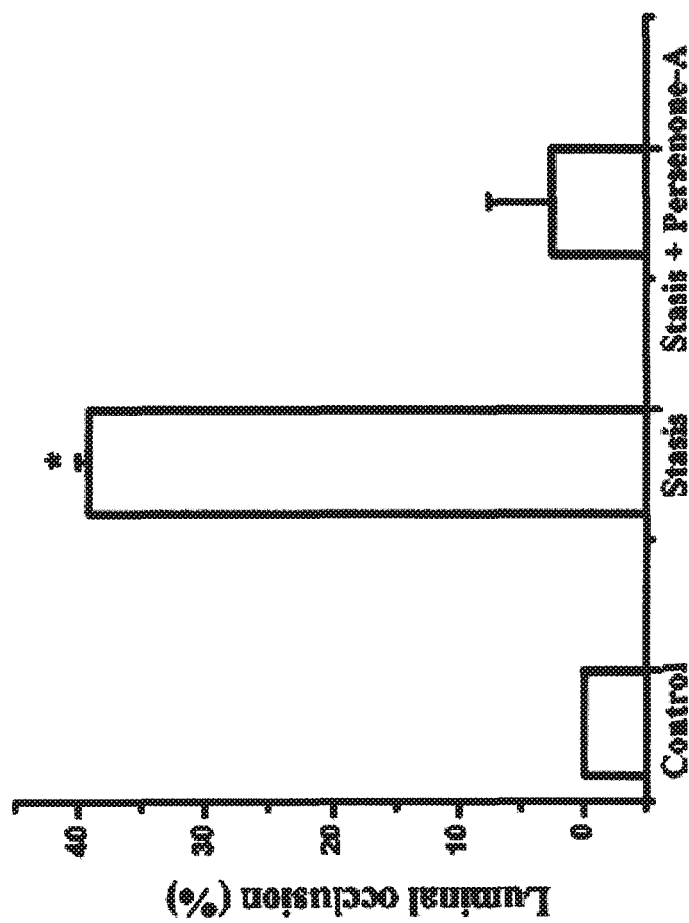
FIG. 5D is a graph showing the percentage of luminal occlusion for in vivo treatment groups in an experimental thrombosis model test, according to a specific example embodiment of the disclosure.

FIG. 5A shows a transverse section of the femoral vasculonervous package stained with Masson's trichome of a mouse femoral artery that does not present thrombi (control). As seen in FIG. 5D, the control group had 0% luminal occlusion. FIG. 5B shows a transverse section of the femoral vasculonervous package stained with Masson's trichome of a mouse femoral artery that has surgical induction of the thrombus (stasis). A recent unorganized thrombus can be observed in the artery. FIG. 5C shows a transverse section of the femoral vasculonervous package stained with Masson's trichonie of a mouse femoral artery that has surgical induction of the thrombus (stasis) after treatment with Persenone-A. As shown in FIG. 5D, the stasis group had approximately 40% luminal occlusion. The group treated with Persenone-A (FIG. 5C) showed a 71% decrease in luminal occlusion compared to the stasis group (FIG. 5D). Thus, the experimental thrombosis model test confirmed the antithrombic effect of Persenone-A.

Example 7: Bioactivity of Acetogenins

Figure 6A:
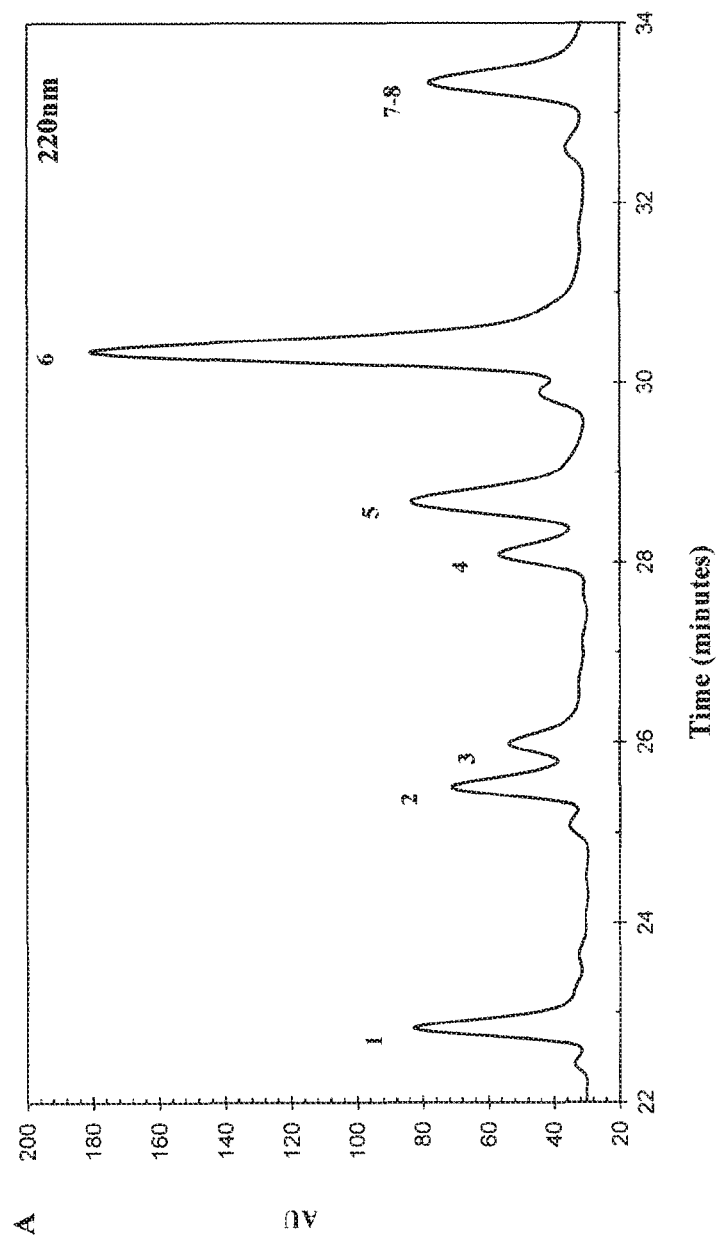
FIG. 6A, illustrates an HPLC chromatogram identifying an acetogenin profile in avocado.
Figure 6B:
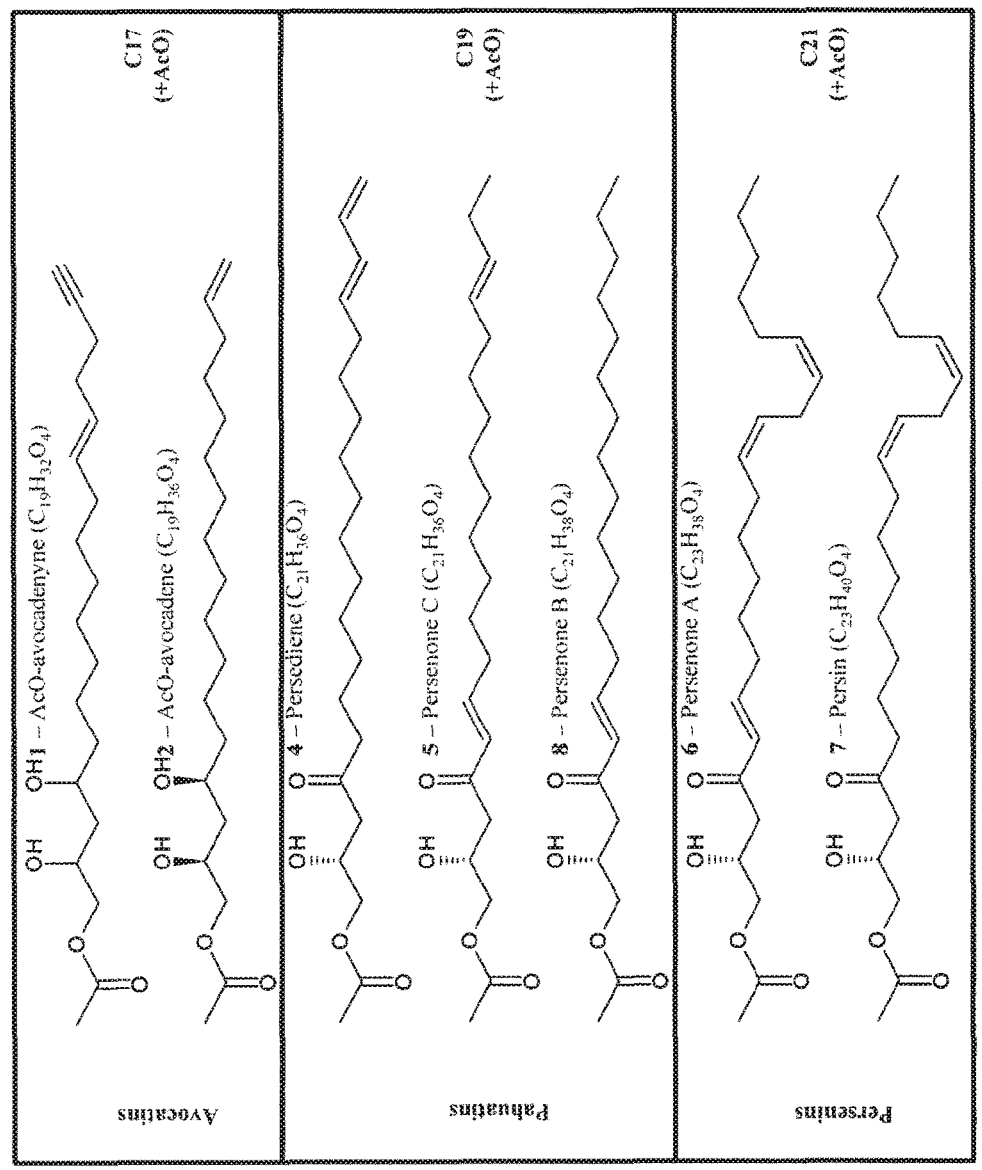
FIG. 6B illustrates the chemical structures of acetogenin molecules identified from the HPLC chromatogram peaks of FIG. 6A.

FIG. 6A, illustrates an HPLC chromatogram identifying an acetogenin profile in avocado fruit. FIG. 6B illustrates the chemical structures of acetogenin molecules identified from the HPLC chromatogram peaks of FIG. 6A. The chemical structures shown in FIG. 6B were confirmed by NMR.

Example 8: Bioactivity of Acetogenins

Acetogenins isolated according to the methods of Example 2 and 3 may be combined in the formulations as shown in Table 3 below. These compositions may be subjected to in vivo assays according to Example 6.

TABLE 3

Examples of compositions containing avocado acetogenins obtained from avocado

| Compounds | COMPOSITION 1 Concentration (g/ 100 g extract) | COMPOSITION 2 Concentration (g/ 100 g extract) |
|---|---|---|
| 1-acetoxy-Avocadenyne ($C_{19}H_{32}O_4$) | 3.53 | 0.88 |
| 1-acetoxy-Avocadene ($C_{19}H_{32}O_4$) | 21.9 | 5.47 |
| Persediene ($C_{21}H_{36}O_4$) | 1.85 | 0.46 |
| Persenone C ($C_{21}H_{36}O_4$) | 3.67 | 0.92 |
| Persenone A ($C_{23}H_{38}O_4$) | 20.44 | 5.11 |
| Persenone B ($C_{21}H_{36}O_4$) | 11.4 | 2.85 |
| Persin ($C_{23}H_{38}O_4$) | 8.53 | 2.13 |
| Total Acetogenins | 71.32 | 17.83 |
| Other avocado lipids | 28.68 | 7.17 |
| Percent Propylene glycol (CAS-No 57-55-6) | 0 | 75 |
| Sum of Composition | 100 | 100 |

What is claimed is:

1. A method of treating or preventing platelet aggregation and/or thrombus formation in a subject, said method comprising:
    selecting a subject in need of, or susceptible to needing, antiplatelet and/or antithrombic treatment; and
    administering an acetogenin selected from the group consisting of Acetogenin 1, Acetogenin 2, Acetogenin 3, Acetogenin 4, Acetogenin 5, Acetogenin 6, Acetogenin 7, Acetogenin 8, Acetogenin 9, Acetogenin 10, Acetogenin 11, Acetogenin 12, Acetogenin 13, and Acetogenin 14, or combinations thereof, to the selected subject to treat or prevent platelet aggregation and/or thrombus formation.

2. The method of claim 1, wherein said method is carried out to treat platelet aggregation and/or thrombus formation.

3. The method of claim 1, wherein said method is carried out to prevent platelet aggregation and/or thrombus formation.

4. The method of claim 1, wherein the compound has the formula:

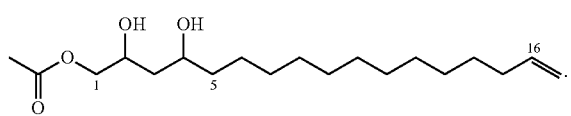

(Acetogenin 1)

5. The method of claim 1, wherein the compound has the formula:

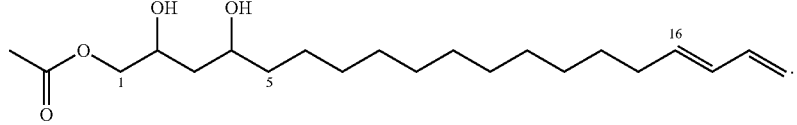

(Acetogenin 2)

6. The method of claim 1, wherein the compound has the formula:

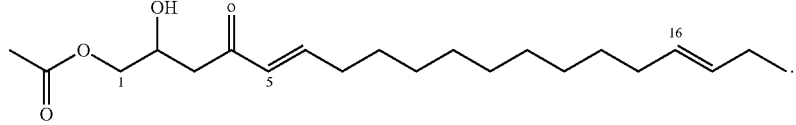

(Acetogenin 3)

7. The method of claim 1, wherein the compound has the formula:

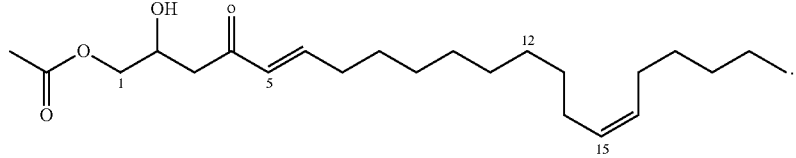

(Acetogenin 4)

8. The method of claim 1, wherein said administering is carried out orally, parenterally, buccally, intraarterially, intracardially, intravenously, intraparietally, intrapulmonarily, sublingually, topically, transdermally, intranasally, intraarticularly, intraosseously, or using combinations thereof.

9. The method of claim 1, wherein the compound is applied as a component of a pharmaceutical composition, said pharmaceutical composition further comprising:
a pharmaceutically acceptable agent.

10. The method of claim 9, wherein the pharmaceutically acceptable agent comprises a carrier, an excipient, an enhancer, a solvent, a diluent, an adjuvant, an additive, or any combination thereof.

11. The method of claim 10, wherein the solvent is selected from the group consisting of water, ethanol, propylene glycol, polyethylene glycol, dimethyl sulfoxide, and combinations thereof.

12. The method according to claim 9, wherein the pharmaceutical composition further comprises:
a salt, a buffer, a sugar, an amino acid, and combinations thereof.

13. The method according to claim 9, wherein the pharmaceutical composition is configured in a dosage form selected from the group consisting of a tablet, a pill, a granule, a powder, a cachet, a solution, a suspension, an emulsion, a syrup, an aerosol, a gelatin capsule, and a powder.

14. The method of claim 1, wherein a combination of the acetogenins is administered to the selected subject.

* * * * *

UNITED STATES PATENT AND TRADEMARK OFFICE
CERTIFICATE OF CORRECTION

PATENT NO. : 10,493,057 B2
APPLICATION NO. : 15/580933
DATED : December 3, 2019
INVENTOR(S) : Hernández Brenes et al.

Page 1 of 1

It is certified that error appears in the above-identified patent and that said Letters Patent is hereby corrected as shown below:

In the Claims

In Claim 5, at Column 23, Line 28, delete "

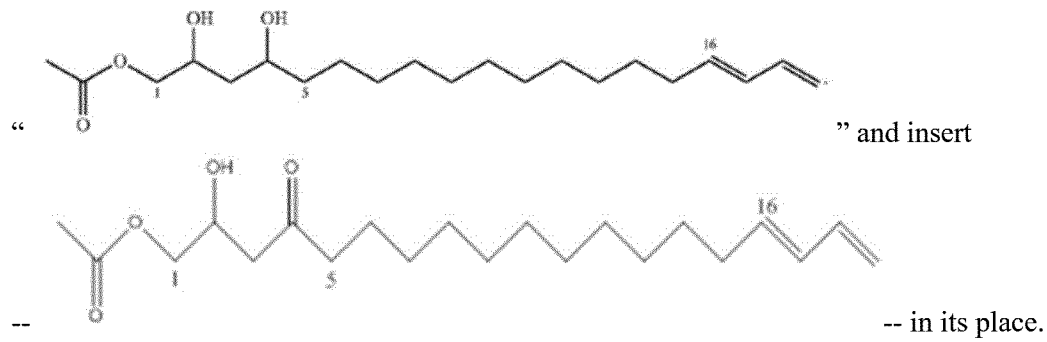

" and insert

-- in its place.

Signed and Sealed this
Twenty-fourth Day of November, 2020

Andrei Iancu
*Director of the United States Patent and Trademark Office*